United States Patent
Libbus et al.

(10) Patent No.: US 9,643,011 B2
(45) Date of Patent: May 9, 2017

(54) IMPLANTABLE NEUROSTIMULATOR-IMPLEMENTED METHOD FOR MANAGING TACHYARRHYTHMIC RISK DURING SLEEP THROUGH VAGUS NERVE STIMULATION

(71) Applicant: CYBERONICS, INC., Houston, TX (US)

(72) Inventors: Imad Libbus, St. Paul, MN (US); Badri Amurthur, Los Gatos, CA (US); Bruce H. Kenknight, Maple Grove, MN (US)

(73) Assignee: CYBERONICS, INC., Houston, TX (US)

( * ) Notice: Subject to any disclaimer, the term of this patent is extended or adjusted under 35 U.S.C. 154(b) by 528 days.

(21) Appl. No.: 13/828,486

(22) Filed: Mar. 14, 2013

(65) Prior Publication Data
US 2014/0277232 A1    Sep. 18, 2014

(51) Int. Cl.
A61N 1/00 (2006.01)
A61N 1/362 (2006.01)
A61N 1/36 (2006.01)

(52) U.S. Cl.
CPC ........ *A61N 1/3621* (2013.01); *A61N 1/36114* (2013.01)

(58) Field of Classification Search
CPC .......................... A61N 1/36114; A61N 1/3621
(Continued)

(56) References Cited

U.S. PATENT DOCUMENTS

| 5,522,854 A | 6/1996 | Ideker et al. |
| 5,707,400 A | 1/1998 | Terry, Jr. et al. |

(Continued)

FOREIGN PATENT DOCUMENTS

| WO | WO9321824 | 11/1993 |
| WO | 03018113 | 3/2003 |

(Continued)

OTHER PUBLICATIONS

US 8,315,702, 11/2012, Chavan et al. (withdrawn)
(Continued)

*Primary Examiner* — Lindsey G Hankins
(74) *Attorney, Agent, or Firm* — Foley & Lardner LLP

(57) ABSTRACT

A patient suffering from congestive heart failure is at increased risk of cardiac arrhythmogenesis during sleep, particularly if experiencing central sleep apnea as a co-morbidity. Low intensity peripheral neurostimulation therapies that target imbalance of the autonomic nervous system have been shown to improve clinical outcomes. Thus, bi-directional autonomic regulation therapy is delivered to the cervical vagus nerve at an intensity that is insufficient to elicit pathological or acute physiological side effects and without the requirement of an enabling physiological feature or triggering physiological marker. The patient's physiology is monitored to identify periods of sleep. In one embodiment, upon sensing a condition indicative of tachyarrhythmia following a period of bradycardia, as naturally occurs during sleep, an enhanced "boost" dose of bi-directional neural stimulation intended to "break" the tachyarrhythmic condition is delivered. In a further embodiment, the boost dose is delivered upon sensing a physiological pattern indicative of Cheyne-Stokes respiration.

8 Claims, 5 Drawing Sheets

(58) Field of Classification Search
USPC .................................................. 607/2, 14
See application file for complete search history.

(56) References Cited

U.S. PATENT DOCUMENTS

| | | | |
|---|---|---|---|
| 5,928,272 A | 7/1999 | Adkins et al. | |
| 5,978,709 A | 11/1999 | Begemann et al. | |
| 6,006,134 A | 12/1999 | Hill et al. | |
| 6,266,564 B1 | 7/2001 | Hill et al. | |
| 6,354,991 B1 | 3/2002 | Gross et al. | |
| 6,449,507 B1 | 9/2002 | Hill et al. | |
| 6,473,644 B1 | 10/2002 | Terry, Jr. et al. | |
| 6,508,771 B1 | 1/2003 | Padmanabhan et al. | |
| 6,522,926 B1 | 2/2003 | Kieval et al. | |
| 6,600,954 B2 | 7/2003 | Cohen et al. | |
| 6,610,713 B2 | 8/2003 | Tracey | |
| 6,616,624 B1 | 9/2003 | Kieval | |
| 6,622,041 B2 | 9/2003 | Terry, Jr. et al. | |
| 6,652,449 B1 | 11/2003 | Gross et al. | |
| 6,684,105 B2 | 1/2004 | Cohen et al. | |
| 6,690,971 B2 | 2/2004 | Schauerte et al. | |
| 6,712,772 B2 | 3/2004 | Cohen et al. | |
| 6,718,208 B2 | 4/2004 | Hill et al. | |
| 6,838,471 B2 | 1/2005 | Tracey | |
| 6,839,594 B2 | 1/2005 | Cohen et al. | |
| 6,850,801 B2 | 2/2005 | Kieval et al. | |
| 6,862,480 B2 | 3/2005 | Cohen et al. | |
| 6,892,098 B2 | 5/2005 | Ayal et al. | |
| 6,896,651 B2 | 5/2005 | Gross et al. | |
| 6,904,318 B2 | 6/2005 | Hill et al. | |
| 6,907,295 B2 | 6/2005 | Gross et al. | |
| 6,963,773 B2 | 11/2005 | Borschowa et al. | |
| 6,963,779 B1 | 11/2005 | Shankar | |
| 6,985,774 B2 | 1/2006 | Kieval et al. | |
| 7,010,345 B2 | 3/2006 | Hill et al. | |
| 7,072,720 B2 | 7/2006 | Puskas | |
| 7,123,961 B1 | 10/2006 | Kroll et al. | |
| 7,136,705 B1 * | 11/2006 | Park | 607/27 |
| 7,139,607 B1 | 11/2006 | Shelchuk | |
| 7,158,832 B2 | 1/2007 | Kieval et al. | |
| 7,184,828 B2 | 2/2007 | Hill et al. | |
| 7,184,829 B2 | 2/2007 | Hill et al. | |
| 7,189,204 B2 | 3/2007 | Ni et al. | |
| 7,218,964 B2 | 5/2007 | Hill et al. | |
| 7,221,979 B2 | 5/2007 | Zhou et al. | |
| 7,225,017 B1 | 5/2007 | Shelchuk | |
| 7,225,019 B2 | 5/2007 | Jahns et al. | |
| 7,237,320 B2 | 7/2007 | Lam | |
| 7,245,967 B1 | 7/2007 | Shelchuk | |
| 7,260,431 B2 | 8/2007 | Libbus et al. | |
| 7,269,457 B2 | 9/2007 | Shafer et al. | |
| 7,277,761 B2 | 10/2007 | Shelchuk | |
| 7,295,861 B2 | 11/2007 | Cohen et al. | |
| 7,305,265 B2 | 12/2007 | Fukui | |
| 7,321,793 B2 | 1/2008 | Ben Ezra et al. | |
| 7,324,853 B2 | 1/2008 | Ayal et al. | |
| 7,336,997 B2 | 2/2008 | Fukui | |
| 7,346,398 B2 | 3/2008 | Gross et al. | |
| 7,387,603 B2 | 6/2008 | Gross et al. | |
| 7,389,149 B2 | 6/2008 | Rossing et al. | |
| 7,395,119 B2 | 7/2008 | Hagen et al. | |
| 7,403,819 B1 | 7/2008 | Shelchuk et al. | |
| 7,418,292 B2 | 8/2008 | Shafer | |
| 7,452,800 B2 | 11/2008 | Sosnowchik et al. | |
| 7,480,532 B2 | 1/2009 | Kieval et al. | |
| 7,481,759 B2 | 1/2009 | Whitehurst et al. | |
| 7,485,104 B2 | 2/2009 | Kieval | |
| 7,493,167 B2 | 2/2009 | Hussein et al. | |
| 7,499,742 B2 | 3/2009 | Bolea et al. | |
| 7,499,747 B2 | 3/2009 | Kieval et al. | |
| 7,499,748 B2 | 3/2009 | Moffitt et al. | |
| 7,502,650 B2 | 3/2009 | Kieval | |
| 7,542,800 B2 | 6/2009 | Libbus et al. | |
| 7,548,780 B2 | 6/2009 | Libbus et al. | |
| 7,551,958 B2 | 6/2009 | Libbus et al. | |
| 7,561,922 B2 | 7/2009 | Cohen et al. | |
| 7,561,923 B2 | 7/2009 | Libbus et al. | |
| 7,570,999 B2 | 8/2009 | Libbus et al. | |
| 7,582,053 B2 | 9/2009 | Gross et al. | |
| 7,584,004 B2 | 9/2009 | Caparso et al. | |
| 7,587,238 B2 | 9/2009 | Moffitt et al. | |
| 7,606,622 B2 | 10/2009 | Reeve | |
| 7,613,511 B2 | 11/2009 | Wu et al. | |
| 7,613,516 B2 | 11/2009 | Cohen et al. | |
| 7,616,990 B2 | 11/2009 | Chavan et al. | |
| 7,617,003 B2 | 11/2009 | Caparso et al. | |
| 7,623,926 B2 | 11/2009 | Rossing et al. | |
| 7,627,384 B2 | 12/2009 | Ayal et al. | |
| 7,628,750 B2 | 12/2009 | Cohen et al. | |
| 7,630,760 B2 | 12/2009 | Libbus et al. | |
| 7,634,315 B2 | 12/2009 | Cholette | |
| 7,634,317 B2 | 12/2009 | Ben-David et al. | |
| 7,640,057 B2 | 12/2009 | Libbus et al. | |
| 7,647,101 B2 | 1/2010 | Libbus | |
| 7,647,114 B2 | 1/2010 | Libbus | |
| 7,650,190 B2 | 1/2010 | Zhou et al. | |
| 7,657,312 B2 | 2/2010 | Pastore et al. | |
| 7,660,628 B2 | 2/2010 | Libbus et al. | |
| 7,664,548 B2 | 2/2010 | Amurthur et al. | |
| 7,668,602 B2 | 2/2010 | Ben-David et al. | |
| 7,672,733 B2 | 3/2010 | Zhou et al. | |
| 7,676,275 B1 | 3/2010 | Farazi et al. | |
| 7,689,286 B2 | 3/2010 | Pastore et al. | |
| 7,711,415 B1 | 5/2010 | Farazi et al. | |
| 7,711,421 B2 | 5/2010 | Shafer et al. | |
| 7,734,355 B2 | 6/2010 | Cohen et al. | |
| 7,751,884 B2 | 7/2010 | Ternes et al. | |
| 7,769,442 B2 | 8/2010 | Shafer | |
| 7,769,446 B2 | 8/2010 | Moffit et al. | |
| 7,778,702 B2 | 8/2010 | Ben-David et al. | |
| 7,778,703 B2 | 8/2010 | Gross et al. | |
| 7,778,711 B2 | 8/2010 | Ben-David et al. | |
| 7,783,353 B2 | 8/2010 | Libbus et al. | |
| 7,797,041 B2 | 9/2010 | Libbus et al. | |
| 7,801,603 B2 | 9/2010 | Westlund et al. | |
| 7,801,604 B2 | 9/2010 | Brockway et al. | |
| 7,801,614 B2 | 9/2010 | Rossing et al. | |
| 7,805,193 B2 | 9/2010 | Libbus et al. | |
| 7,805,203 B2 | 9/2010 | Ben-David | |
| 7,813,805 B1 | 10/2010 | Farazi | |
| 7,813,812 B2 | 10/2010 | Kieval et al. | |
| 7,835,797 B2 | 11/2010 | Rossing et al. | |
| 7,840,266 B2 | 11/2010 | Libbus et al. | |
| 7,840,271 B2 | 11/2010 | Kieval et al. | |
| 7,844,346 B2 | 11/2010 | Cohen et al. | |
| 7,848,812 B2 | 12/2010 | Crowley et al. | |
| 7,848,816 B1 | 12/2010 | Wenzel et al. | |
| 7,869,869 B1 | 1/2011 | Farazi | |
| 7,885,709 B2 | 2/2011 | Ben-David | |
| 7,885,711 B2 | 2/2011 | Ben-Ezra et al. | |
| 7,890,185 B2 | 2/2011 | Cohen et al. | |
| 7,894,907 B2 | 2/2011 | Cowan et al. | |
| 7,904,151 B2 | 3/2011 | Ben-David | |
| 7,904,175 B2 | 3/2011 | Scott et al. | |
| 7,904,176 B2 | 3/2011 | Ben-Ezra et al. | |
| 7,908,008 B2 | 3/2011 | Ben-David et al. | |
| 7,916,013 B2 | 3/2011 | Stevenson | |
| 7,925,342 B2 | 4/2011 | Amurthur et al. | |
| 7,925,352 B2 | 4/2011 | Stack et al. | |
| 7,974,693 B2 | 7/2011 | Ben-David et al. | |
| 8,005,542 B2 | 8/2011 | Ben-Ezra et al. | |
| 8,005,545 B2 | 8/2011 | Ben-David et al. | |
| 8,036,745 B2 | 10/2011 | Ben-David et al. | |
| 8,060,197 B2 | 11/2011 | Ben-David et al. | |
| 8,065,021 B2 | 11/2011 | Gross et al. | |
| 8,083,663 B2 | 12/2011 | Gross et al. | |
| 8,116,881 B2 | 2/2012 | Cohen et al. | |
| 8,131,362 B2 | 3/2012 | Moffitt et al. | |
| 8,160,701 B2 | 4/2012 | Zhao et al. | |
| 8,160,705 B2 | 4/2012 | Stevenson et al. | |
| 8,195,290 B2 | 6/2012 | Brockway | |
| 8,224,436 B2 | 7/2012 | Libbus et al. | |
| 8,249,711 B2 | 8/2012 | Libbus et al. | |
| 8,369,943 B2 | 2/2013 | Shuros et al. | |

(56) References Cited

U.S. PATENT DOCUMENTS

| | | | |
|---|---|---|---|
| 8,386,038 B2 | 2/2013 | Bianchi et al. | |
| 8,401,640 B2 | 3/2013 | Zhao et al. | |
| 8,417,354 B2 | 4/2013 | Zhang et al. | |
| 8,571,654 B2 | 10/2013 | Libbus et al. | |
| 8,577,458 B1 | 11/2013 | Libbus et al. | |
| 8,600,505 B2 | 12/2013 | Libbus et al. | |
| 8,634,921 B2 | 1/2014 | Chavan et al. | |
| 8,688,212 B2 | 4/2014 | Libbus et al. | |
| 2002/0107553 A1 | 8/2002 | Hill et al. | |
| 2003/0040774 A1 | 2/2003 | Terry et al. | |
| 2003/0153954 A1 | 8/2003 | Park et al. | |
| 2003/0171781 A1 | 9/2003 | Florio et al. | |
| 2004/0199210 A1 | 10/2004 | Shelchuk | |
| 2004/0210261 A1* | 10/2004 | King et al. | 607/9 |
| 2004/0215265 A1 | 10/2004 | Keizer | |
| 2005/0049655 A1 | 3/2005 | Boveja et al. | |
| 2005/0065553 A1 | 3/2005 | Ben Ezra et al. | |
| 2005/0125044 A1 | 6/2005 | Tracey | |
| 2005/0131467 A1 | 6/2005 | Boveja | |
| 2005/0165465 A1* | 7/2005 | Pianca et al. | 607/116 |
| 2005/0267542 A1 | 12/2005 | David et al. | |
| 2006/0100668 A1 | 5/2006 | Ben-David et al. | |
| 2006/0190053 A1 | 8/2006 | Dobak, III | |
| 2006/0206155 A1 | 9/2006 | Ben-David et al. | |
| 2006/0253161 A1 | 11/2006 | Libbus et al. | |
| 2007/0067004 A1 | 3/2007 | Boveja et al. | |
| 2007/0093870 A1 | 4/2007 | Maschino et al. | |
| 2007/0179543 A1 | 8/2007 | Ben-David et al. | |
| 2007/0213773 A1 | 9/2007 | Hill et al. | |
| 2007/0233194 A1 | 10/2007 | Craig | |
| 2007/0255320 A1 | 11/2007 | Inman et al. | |
| 2007/0276453 A1 | 11/2007 | Hill et al. | |
| 2008/0015659 A1 | 1/2008 | Zhang et al. | |
| 2008/0021503 A1 | 1/2008 | Whitehurst et al. | |
| 2008/0033511 A1 | 2/2008 | Dobak | |
| 2008/0051839 A1 | 2/2008 | Libbus et al. | |
| 2008/0058874 A1 | 3/2008 | Westlund et al. | |
| 2008/0061240 A1 | 3/2008 | Heuft | |
| 2008/0091240 A1 | 4/2008 | Ben-David et al. | |
| 2008/0132983 A1 | 6/2008 | Cohen et al. | |
| 2008/0147140 A1 | 6/2008 | Ternes et al. | |
| 2008/0183258 A1 | 7/2008 | Inman | |
| 2008/0243196 A1 | 10/2008 | Libbus et al. | |
| 2008/0319513 A1 | 12/2008 | Pu et al. | |
| 2009/0030493 A1 | 1/2009 | Colburn et al. | |
| 2009/0118777 A1 | 5/2009 | Iki et al. | |
| 2009/0124848 A1 | 5/2009 | Miazga | |
| 2009/0149900 A1 | 6/2009 | Moffitt et al. | |
| 2009/0248097 A1 | 10/2009 | Tracey et al. | |
| 2009/0270953 A1 | 10/2009 | Ecker et al. | |
| 2009/0275956 A1 | 11/2009 | Burnes et al. | |
| 2010/0010556 A1 | 1/2010 | Zhao et al. | |
| 2010/0010603 A1 | 1/2010 | Ben-David et al. | |
| 2010/0016919 A1 | 1/2010 | Hill et al. | |
| 2010/0042173 A1 | 2/2010 | Farazi et al. | |
| 2010/0114197 A1 | 5/2010 | Burnes et al. | |
| 2010/0114203 A1 | 5/2010 | Burnes et al. | |
| 2010/0114227 A1 | 5/2010 | Cholette | |
| 2010/0174341 A1 | 7/2010 | Bolea et al. | |
| 2010/0286740 A1 | 11/2010 | Libbus et al. | |
| 2010/0331908 A1* | 12/2010 | Farazi | 607/17 |
| 2011/0015692 A1 | 1/2011 | Libbus et al. | |
| 2011/0082514 A1 | 4/2011 | Libbus et al. | |
| 2011/0098796 A1 | 4/2011 | Ben-David et al. | |
| 2011/0224749 A1 | 9/2011 | Ben-David et al. | |
| 2011/0257708 A1 | 10/2011 | Kramer et al. | |
| 2011/0313488 A1 | 12/2011 | Hincapie Ordonez et al. | |
| 2012/0143286 A1 | 6/2012 | Hahn et al. | |
| 2012/0172742 A1 | 7/2012 | Arcot-Krishnamurthy et al. | |
| 2012/0185007 A1 | 7/2012 | Ziegler et al. | |
| 2012/0185010 A1 | 7/2012 | Zhou et al. | |
| 2012/0192874 A1 | 8/2012 | Bolea et al. | |
| 2012/0271374 A1 | 10/2012 | Nelson et al. | |
| 2012/0303080 A1 | 11/2012 | Ben-David et al. | |
| 2013/0158616 A1 | 6/2013 | Libbus et al. | |
| 2013/0158617 A1 | 6/2013 | Libbus et al. | |
| 2013/0158618 A1 | 6/2013 | Libbus et al. | |
| 2013/0238047 A1 | 9/2013 | Libbus et al. | |
| 2013/0289646 A1 | 10/2013 | Libbus et al. | |
| 2014/0135862 A1 | 5/2014 | Libbus et al. | |
| 2014/0135863 A1 | 5/2014 | Libbus et al. | |
| 2014/0135864 A1 | 5/2014 | Libbus et al. | |
| 2014/0228905 A1 | 8/2014 | Bolea | |
| 2015/0073511 A1 | 3/2015 | Libbus et al. | |
| 2015/0073512 A1 | 3/2015 | Libbus et al. | |
| 2015/0094962 A1 | 4/2015 | Hoegh et al. | |
| 2015/0119956 A1 | 4/2015 | Libbus et al. | |
| 2015/0119959 A1 | 4/2015 | Libbus et al. | |
| 2015/0196762 A1 | 7/2015 | Amurthur et al. | |

FOREIGN PATENT DOCUMENTS

| | | |
|---|---|---|
| WO | 03099373 | 12/2003 |
| WO | 03099377 | 12/2003 |
| WO | 2004110549 | 12/2004 |
| WO | 2004110550 | 12/2004 |
| WO | 2005011805 | 2/2005 |
| WO | 2006019764 | 2/2006 |
| WO | WO2010005482 A1 | 1/2010 |

OTHER PUBLICATIONS

PCT Application No. PCT/US2013/068541, International Preliminary Report on Patentability dated May 21, 2015, 9 pages.
PCT Application No. PCT/US2013/050390, Search Report and Written Opinion dated Nov. 5, 2013.
PCT Application No. PCT/US2013/068541, Search Report and Written Opinion dated Jan. 7, 2014.
PCT Application No. PCT/US2012/068205, Search Report and Written Opinion dated Feb. 8, 2013, 15 pages.
PCT Application No. PCT/US2012/068213, Search Report and Written Opinion dated Mar. 15, 2013, 11 pages.
PCT Application No. PCT/US2012/068223, Search Report and Written Opinion dated Apr. 3, 2013, 11 pages.
PCT Application No. PCT/US2013/021964, Search Report and Written Opinion dated Apr. 17, 2013, 10 pages.
PCT Application No. PCT/US2012/068211, Search Report and Written Opinion dated May 7, 2013, 9 pages.
Abraham, et al., "Devices in the management of advanced, chronic heart failure," Nature Reviews, vol. 10, pp. 98-110 (Feb. 2013) (Published online Dec. 11, 2012).
Adamson, et al., "Continuous Autonomic Assessment in Patients with Symptomatic Heart Failure: Prognostic Value of Heart Rate Variability Measured by an Implanted Cardiac Resynchronization Device," Circulation, Journal of the American Heart Association, 110, pp. 2389-2394 (2004).
Agostoni, et al., "Functional and Histological Studies of the Vagus Nerve and its Branches to the Heart, Lungs and Abdominal Viscera in the Cat," J. Physiol. 135, pp. 182-205 (1957).
Ajani, et al., "Prevalence of High C-Reactive Protein in Persons with Serum Lipid Concentrations within Recommended Values," Chemical Chemistry, 50:9, pp. 1618-1622 (2004).
Akiyama, et al., "Effects of right and left vagal stimulation on left ventricular acetylcholine levels in the cat," Acta Physiol Scand, 172, pp. 11-16 (2001).
Anand, et al., "C-Reactive Protein in Heart Failure: Prognostic Value and the Effect of Valsartan," Circulation, Journal of the American Heart Association, 112, pp. 1428-1434 (2005).
Anholt, et al., "Recruitment and blocking properties of the CardioFit stimulation lead," Journal of Neural Engineering, 8, pp. 1-6, (2011).
Ardell, et al., "Selective vagal innervation of sinoatrial and atrioventricular nodes in canine heart," Am. J. Physiol. 251 (Heart Circ. Physiol. 20), pp. H764-H773 (1986).
Armour, "Cardiac neuronal hierarchy in health and disease," Am J Physiol Regul Integr Comp Physiol, 287, pp. R262-R271 (2004).
Armour, "Myocardial ischaemia and the cardiac nervous system," Cardiovascular Research, 41, pp. 41-54 (1999).
Armour, JA, "Potential clinical relevance of the 'little brain' on the mammalian heart," Experimental Physiology, vol. 1 93, No. 2, pp.

(56) References Cited

OTHER PUBLICATIONS 165-176 (Feb. 2008). Online Publication Date: Nov. 2, 2007. Available at: http://ep.physoc.org/ content/93/2/165.long.
Armour, "The little brain on the heart," Cleveland Clinic Journal of Medicine, vol. 74, supp. 1, pp. S48-S51 (Feb. 2007).
Armour, et al., "Functional anatomy of canine cardiac nerves," Acta anat., 91, pp. 510-528 (1975).
Armour, et al., "Localized myocardial responses to stimulation of small cardiac branches of the vagus," American Journal of Physiology, vol. 228, No. 1 pp. 141-148 (Jan. 1975).
Asala, et al., "An electron microscope study of vagus nerve composition in the ferret," Anat Embryol, 175, pp. 247-253 (1986).
Aukrust, et al., "Inflammatory and anti-inflammatory cytokines in chronic heart failure: Potential therapeutic implications," Annals of Medicine, 37, pp. 74-85 (2005).
Author Unknown, "Nerve fiber—Types and Function," www.boddunan.com Available at ww.boddunan.com/education/20-medicine-a-surgery/12730-nerver-fiber-types-and-function.html (Apr. 19, 2010).
Author Unknown, American Diabetes Association, "Standards of Medical Care in Diabetes—2012," Diabetes Care, vol. 35, supplement 1, pp. S11-S63 (Jan. 2012).
Author Unknown, Staff of Adinstruments, "Principles of Nerve Stimulation," Application Note, ADInstruments (Apr. 2002).
Bae, et al., "Gliosis in the Amygdala Following Myocardial Infarction in the Rat," J Vet Med Sci, 72(8), pp. 1041-1045 (2010).
Bernik, et al., "Pharmacological Stimulation of the Cholinergic Antiinflammatory Pathway," J. Exp. Med, vol. 195, No. 6, pp. 781-788 (Mar. 18, 2002).
Berthoud, et al., "Functional and chemical anatomy of the afferent vagal system," Autonomic Neuroscience: Basic and Clinical, 85, pp. 1-17 (2000).
Bhagat, et al., "Differential Effect of Right and Left Vagal Stimulation on Right and Left Circumflex Coronary Arteries," S A Medical Journal, 50, pp. 1591-1594 (1976).
Biasucci, et al., "Elevated Levels of C-Reactive Protein at Discharge in Patients with Unstable Angina Predict Recurrent Instability," Circulation,Journal of the American Heart Association, 99, pp. 855-860 (1999).
Bibevski, et al., "Evidence for impaired vagus nerve activity in heart failure," Heart Fail Rev, 16, pp. 129-135 (2011).
Bibevski, et al., "Ganglionic Mechanisms Contribute to Diminished Vagal Control in Heart Failure," Circulation, Journal of the American Heart Association, 99, pp. 2958-2963 (1999).
Bilgutay, et al., "Vagal Tuning A new concept in the treatment of supraventricular arrhythmias, angina pectoris, and heart failure," Journal of Thoracic and Cardiovascular Surgery, vol. 56, No. 1, pp. 71-82 (Jul. 1968).
Binkley, et al., "Parasympathetic Withdrawal Is an Integral Component of Autonomic Imbalance in Congestive Heart Failure Demonstration in Human Subjects and Verification in a Paced Canine Model of Ventricular Failure," JACC, vol. 18, No. 2, pp. 464-472 (Aug. 1991).
Bois, et al., "Mode of action of bradycardic agent, S 16257, on ionic currents of rabbit sinoatrial node cells," Abstract, British Journal of Pharmacology, 118(4):1051-7 (1996).
Bonaz, et al., "Vagus nerve stimulation: From epilepsy to the cholinergic anti-inflammatory pathway," Neurogastroenterology & Motility, pp. 1-14 (2013).
Borggrefe, et al., "Vagal Stimulation Devices," ESC Congress 2010 (2010).
Borovilkova, et al., "Vagus nerve stimulation attenuates the systemic inflammatory response to endotoxin," Nature, vol. 405, pp. 458-462 (May 25, 2000).
Brack, et al., "Mechanisms underlying the autonomic modulation of ventricular fibrillation initiation—tentative prophylactic properties in vagus nerve stimulation on malignant arrhythmias in heart failure," Heart Fail Rev (Published online Jun. 8, 2012).
Bronzino, "Biomedical Engineering Fundamentals," CRC Press, Chapter 30, pp. 30-10-30-15 (Apr. 2006).
Buschman, et al., "Heart Rate Control Via Vagus Nerve Stimulation," Neuromodulation, vol. 9, No. 3, pp. 214-220 (2006).
Butterwick, et al .,"Tissue Damage by Pulsed Electrical Stimulation," IEEE Transactions on Biomedical Engineering, vol. 54, No. 12, pp. 2261-2267 (Dec. 2007).
Calkins, et al., "Comparison of Responses to Isoproterenol and Epinephrine During Head-Up Tilt in Suspected Vasodepressor Syncope," The American Journal of Cardiology, vol. 67 pp. 207-209 (Jan. 15, 1991).
Castoro, et al., "Excitation properties of the right cervical vagus nerve in adult dogs," Experimental Neurology, 227 (pp. 62-68 (2011).
Castoro et al.,"Excitation properties of the right cervical vagus nerve in adult dogs," Experimental Neurology, vol. 2 227, iss. 1, pp. 62-68 (Jan. 2011). Online Publication Date: Sep. 17, 2010. Available at: http://www.sciencedirecl.com/science/article/pii/ 5001448861000347X.
Chapleau, et al., "Methods of assessing vagus nerve activity and reflexes," Heart Fail Rev, 16, pp. 109-127 (2011).
Chen, et al., "National and Regional Trends in Heart Failure Hospitalization and Mortality Rates for Medicare Beneficiaries, 1998-2008," JAMA, vol. 306, No. 15 (Oct. 19, 2011).
Chen, et al., "Role of Atrial Electrophysiology and Autonomic Nervous System in Patients with Supraventricular Tachycardia and Paroxysmal Artrial Fibrillation," J Am Coll Cardiol, vol. 32, No. 3, pp. 732-738 (Sep. 1998).
Cheng, et al., "Long-term Outcomes in Individuals with Prolonged PR Interval or First-Degree Atrioventricular Block," JAMA, vol. 301, No. 24 pp. 2571-2577 (Jun. 24, 2009).
Chiou, et al., "Effects of Continuous Enhanced Vagal Tone and Dual Atrioventricular Node and Accessory Pathways," Circulation, Journal of the American Heart Association, 107, pp. 2583-2588 (2003).
Cohen, et al., "Histopathology of the stimulated Vagus nerve: Primum non nocere," Heart Fail Rev, 16, pp. 163-169 (2011).
Colombo, et al., "Comparison between spectral analysis and the phenylephrine methods for the assessment of baroreflex sensitivity in chronic heart failure," Clinical Science, 97, pp. 503-513 (1999).
Cryan, et al., "Animal models and mood disorders: recent developments," Current Opinion in Psychiatry, 20, pp. 1-7 (2007).
Das, "Vagal nerve stimulation in prevention and management of coronary heart disease," World J. Cardiol, 3(4), pp. 105-110 (Apr. 26, 2011).
De Castro, et al., "Parasympathetic-mediated atrial fibrillation during tilt test associated with increased baroreflex sensitivity," The European Society of Cardiology, Europace, 8, pp. 349-351 (2006).
De Ferrari, et al., "Baroreflex Sensitivity Predicts Long-Term Cardiovascular Mortality After Myocardial Infarction Even in Patients with Preserved Left Ventricular Function," Journal of the American College of Cardiology, vol. 50, No. 24, pp. 2285-2290 (2007).
De Ferrari, et al., "Chronic Vagal Stimulation in Patients with Congestive Heart Failure," 31st Annual International Conference of the IEE EMBS (2009).
De Ferrari, et al., "Chronic vagus nerve stimulation: a new and promising therapeutic approach for chronic heart failure," European Heart Journal, 32, pp. 847-855 (2011).
De Ferrari et al., "Chronic vagus nerve stimulation: a new and promising therapeutic approach for chronic heart failure," European Heart Journal, vol. 32, iss. 7, pp. 847-855 (Apr. 2011). Online publication date: Oct. 28, 2010. Available at: http://eurheartj. oxfordjournals.org/content/3217/84 7.long.
De Ferrari, et al., "Vagus nerve stimulation: from pre-clinical to clinical application: challenges and future directions," Heart Fail Rev, 16, pp. 195-203 (2011).
De Jonge, et al., "Stimulation of the vagus nerve attenuates macrophage activation by activating the Jak2-STAT3 signaling pathway," Nature Immunology, vol. 6, No. 8, pp. 844-852 (Aug. 2005).
Desai, et al., "Pharmacologic modulation of parasympathetic activity in heart failure," Heart Fail Rev, 16, pp. 179-193 (Published online: Oct. 6, 2010) (2011).
Dickerson, et al., "Parasympathetic neurons in the cranial medial ventricular fat pad on the dog heart selectively decrease ventricular contractility," Journal of the Autonomic Nervous System, 70, pp. 129-141 (1998).

(56) References Cited

OTHER PUBLICATIONS

Dunlap, et al., "Mechanisms of altered vagal control in heart failure: influence of muscarinic receptors and acetylcholinesterase activity," Am J Physiol Heart Circ Physiol, 285, pp. H1632-H1640 (Jun. 26, 2003).
Elsenbruch, et al., "Heart Rate Variability During Waking and Sleep in Healthy Males and Females," SLEEP, vol. 22, No. 8, pp. 1067-1071 (1999).
Euler, et al., "Acetylcholine release by a stimulus train lowers atrial fibrillation threshold," Am. J Physiol. 253 (Heart Circ. Physiol, 22), pp. H863-H868 (1987).
Evans, et al., "Histological and functional studies on the fibre composition of the vagus nerve of the rabbit," Journal of Anatomy, 130, pp. 139-151 (1954).
Fallen, "Vagal Afferent Stimulation as a Cardioprotective Strategy? Introducing the Concept," A.N.E., vol. 10, No. 4 (Oct. 2005).
Fan, et al., "Transvenous vagus nerve stimulation: A potential heart failure therapy is feasible in humans," JACC, vol. 55, issue 10A, pp. E152-E153 (2010).
Fazan, et al., "Diabetic Peripheral Neuropathies: A Morphometric Overview," Int. J. Morphol, 28(I), pp. 51-64 (2010).
Feinauer, et al., "Ouabain enhances release of acetylcholine in the heart evoked by unilateral vagal stimulation," Arch Pharmacol, 333, pp. 7-12 (1986).
Fonarow, et al., "Incremental Reduction in Risk of Death Associated with Use of Gudeline-Recommended Therapies in Patients with Heart Failure: A Nested Case-Control Analysis of Improve HF," J Am Heart Assoc, 1, pp. 16-26 (2012).
Ford, et al., "The effects of electrical stimulation of myelinated and non-myelinated vagal fibres on heart rate in the rabbit," J. Physiol. 380, pp. 341-347 (1986).
Furukawa, et al., "Effects of Verapamil, Zatebradine, and E-4031 on the Pacemaker Location and Rate in Response to Sympathetic Stimulation in Dog Hearts," The Journal of Pharmacology and Experimental Therapeutics, vol. 289, No. 3, pp. 1334-1342 (1999).
Furukawa, et al., "Selective inhibition by zatebradine and discrete parasympathetic stimulation of the positive chronotropic response to sympathetic stimulation in anesthetized dogs," Abstract, Journal of Pharmacology & Experimental Therapeutics, 272(2):744-9 (1995).
Gatti, et al., "Can neurons in the nucleus ambiguus selectively regulate cardiac rate and atrio-ventricular conduction?" Journal of the Autonomic Nervous System, 57, pp. 123-127 (1996).
Gatti, et al., "Vagal control of left ventricular contractility is selectively mediated by a cranioventricular intracardiac ganglion in the cat," Journal of the Autonomic Nervous System, 66, pp. 138-144 (1997).
Gibbons, et al., "Neuromodulation targets intrinsic cardiac neurons to attenuate neuronally mediated atrial arrhythmias," Am J Physiol Regul Integr Comp Physiol 302: R357-R364 (2012) (First published Nov. 16, 2011).
Gottdiener, et al., "Predictors of Congestive Heart Failure in the Elderly: The Cardiovascular Heatlh Study," Journal of the American College of Cardiology, vol. 35, No. 6, pp. 1628-1637 (2000).
Gray, et al., "Parasympathetic control of the Heart. II. A novel interganglionic intrinsic cardiac circuit mediates neural control of heart rate," J. Appl Physiol, 96, pp. 2273-2278 (2004).
Gray, et al., "Parasympathetic control of the Heart. III. Neuropeptide Y-immunoreactive nerve terminals synapse on three populations of negative chronotropic vagal preganglionic neurons," J. Appl Physiol, 96, pp. 2279-2287 (2004).
Grill, "Chapter 14—Principles of Electric Field Generation for Stimulation of the Central Nervous System," Neuromodulation, Academic Press (2009).
Guilleminault, et al., "Cyclical Variation of the Heart Rate in Sleep Apnoea Syndrome," The Lancet, pp. 126-131 (Jan. 21, 1984).
Hardwick, et al., "Chronic myocardial infarction induces phenotypic and functional remodeling in the guinea pig cardiac plexus," Am J Physiol Regulatory Integrative Comp Physiol, 295, pp. 1926-1933 (2008).

Hardwick, et al., "Remodeling of the guinea pig intrinsic cardiac plexus with chronic pressure overload," Am J Physiol Regulatory Integrative Comp Physiol, 297, pp. 859-866 (2009).
Hauptman, et al., "The vagus nerve and autonomic imbalance in heart failure: past, present, and future," Heart Fail Rev, 16, pp. 97-99 (2011).
Hirooka, et al., "Imbalance of central nitric oxide and reactive oxygen species in the regulation of sympathetic activity and neural mechanisms of hypertension," Am J Physiol Regulatory Integration Comp Physiol, 300, pp. 818-826 (2011).
Hoffman, et al., "Vagus Nerve Components," Anat Rec, 127, pp. 551-568 (1957).
Hu, et al., "Role of sympathetic nervous system in myocardial ischemia injury: Beneficial or deleterious?" Letters to the Editor, Elsevier Ireland Ltd. (Mar. 27, 2012).
Hua, et al., "Left vagal stimulation induces dynorphin release and suppresses substance P release from the rat thoracic spinal cord during cardiac ischemia," Am J Physiol Regulatory Integration Comp Physiol, 287, pp. 1468-1477 (2004).
Huston, et al., "Splenectomy inactivates the cholinergic antiinflammatory pathway during lethal endotoxemia and polymicrobial sepsis;" J. Exp. Med, vol. 203, No. 7 pp. 1623-1628 (Jun. 19, 2006).
Huston, et al., "Transcutaneous vagus nerve stimulation reduces serum high mobility group box 1 levels and improves survival in murine sepsis," Crit Care Med, vol. 35, No. 12, pp. 2762-2768 (2007).
Ingemansson, et al., "Autonomic modulation of the atrial cycle length by the head up tilt test: non-invasive evaluation in patients with chronic atrial fibrillation," Heart, 80, pp. 71-76 (1998).
Ito, et al., "Efferent sympathetic and vagal innervation of the canine right ventricle," Circulation, Journal of the American Heart Association, vol. 90, pp. 1469-1468 (1994).
Jacques, et al., "Spinal Cord Stimulation Causes Potentiation of Right Vagus Nerve Effects on Atrial Chronotropic Function and Repolarization in Canines," Journal of Cardiovascular Electrophysiology, vol. 22, No. 4, pp. 440-447 (Apr. 2011).
Jaenisch, et al., "Respiratory muscle training improves baroreceptor sensitivity, decrease sympathetic tonus and increase vagal effect in rats with heart failure," European Heart Journal, 32 (Abstract Supplement, pp. 976 (2011).
Jammes, et al., "Afferent and efferent components of the bronchial vagal branches in cats," Journal of the Autonomic Nervous System, 5, pp. 165-176 (1982).
Janabi, et al., "Oxidized LDL—Induced NF-κB Activation and Subsequent Expression of Proinflammatory Genes are Defective in Monocyte-Derived Macrophages from CD36-Deficient Patients," Arterioscler Thromb Vasc Biol., 20:1953-1960 (2000).
Janse, et al., "Effects of unilateral stellate ganglion stimulation and ablation on electrophysiologic changes induced by acute myocardial ischemia in dogs," Circulation, Journal of the American Heart Association, 72, pp. 585-595 (1985).
Jessup, et al., "2009 Focused Update: ACCF/AHA Guidelines for the Diagnosis and Management of Heart Failure in Adults," Circulation, Journal of the American Heart Association, vol. 119, pp. 1977-2016 (2009).
Johnson, et al., "Parasympathetic control of the heart. I. An interventriculo-septal ganglion is the major source of the vagal intracardiac innervation of the ventricles," J Appl Physiol, 96, pp. 2265-2272 (2004).
Kakinuma, et al., "Cholinoceptive and cholinergic properties of cardiomyocytes involving an amplification mechanism for vagal efferent effects in sparsely innervated ventricular myocardium," FEBS Journal, 276, pp. 5111-5125 (2009).
Kalman, "Specific effects of zatebradine on sinus node function: suppression of automaticity, prolongation of sinoatrial conduction and pacemaker shift in the denervated canine heart," Abstract, Journal of Pharmacology & Experimental Therapeutics, 272(1):85-93 (1995).
Kaneko, et al., "C-Reactive Protein in Dilated Cardiomyopathy," Cardiology, 91, pp. 215-219 (1999).
Katare, et al., "Vagal nerve stimulation prevents reperfusion injury through inhibition of opening of mitochondrial permeability tran-

(56) References Cited

OTHER PUBLICATIONS sition pore independent of bradycardiac effect," The Journal of Thoracic and Cardiovascular Surgery, vol. 137, No. 1, pp. 223-231 (2009).
Katz, et al., "Diseases of the heart in the Works of Hippocrates," Br Heart J, 24, pp. 257-264 (1962).
Kawada, et al., "High-frequency dominant depression of peripheral vagal control of heart rate in rats with chronic heart failure," Acta Physiol 207, 494-502 (2013).
Kawada, et al., "Vagal stimulation suppresses isschemia-induced myocardial interstitial norepinephrine release," Life Sciences, 78, pp. 882-887 (2006).
Kawashima, "The autonomic nervous system of the human heart with special reference to its origin, course, and peripheral distribution," Anat Embryol, 209, pp. 425-438 (2005).
Klein et al., "Vagus nerve stimulation: A new approach to reduce heart failure," Cardiology Journal, vol. 17, iss. 6, pp. 638-643 (2010).
Kliks, et al., "Influence of Sympathetic Tone on Ventricular Fibrillation Threshold During Experimental Coronary Occlusion," The American Journal of Cardiology, vol. 36, pp. 45-49 (Jul. 1975).
Kolman, et al., "The effect of vagus nerve stimulation upon vulnerability of the canine ventricle: role of sympathetic-parasympathetic interactions," Journal of the American Heart Association, 52, pp. 578-585 (1975).
Kong, et al., "Optimizing the Parameters of Vagus Nerve Stimulation by Uniform Design in Rats with Acute Myocardial Infarction," PLOS One, vol. 7, issue 11 (Nov. 2012).
Koopman, et al., "Pilot study of stimulation of the cholinergic anti-inflammatory pathway with an implantable vagus nerve stimulation device in patients with rheumatoid arthritis," Abstract (2012).
Kulbertus, et al., ed., "Neurocardiology," Futura Publishing Co., pp. 13 ("Anatomy of the Cardiac Efferent Innvervation"); 61-63 ("Autonomic Neural Control"); 87, 89, 92-93 ("Sympathetic-Parasympathetic Interactions"); 183, 187 ("Parasympathetic Nervous System"); 104 (1988).
La Rovere, et al., "Baroreflex Sensitivity and Heart Rate Variability in the Identification of Patients at Risk for Life-Threatening Arrhythmias: Implications for Clinical Trials," Circulation, Journal of the American Heart Association, 103, pp. 2072-2077 (2001).
La Rovere, et al., "Baroreflex sensitivity and heart-rate variability in prediction of total cardiac mortality after myocardial infarction. ATRAMI (Autonomic Tone and Reflexes After Myocardial Infarction) Investigators," Lancet, 351(9101), pp. 478-484 (Feb. 14, 1998).
Lane, et al., "Prediction and Prevention of Sudden Cardiac Death in Heart Failure," Heart, 91, pp. 674-680 (2005).
Lechat, et al., "Heart rate and Cardiac Rhythm Relationships with Bisoprolol Benefit in Chronic Heart Failure in CIBIS II Trial," Circulation, Journal of American Heart Association, 103, pp. 1428-1433 (2001).
Lewis, et al., "Vagus nerve stimulation decreases left ventricular contractility in vivo in the human and pig heart," Journal of Physiology, 534, pp. 547-552 (2001).
Li, et al., "Early vagal stimulation markedly prevented cardiac dysfunction in rats after acute myocardial infarction in addition to suppressing arrhythmic death," European Heart Journal, 32 (Abstract Supplement), pp. 297-298 (2011).
Li, et al., "Inflammatory cytokines and nitric oxide in heart failure and potential modulation by vagus nerve stimulation," Heart Fail Rev, 16, pp. 137-145 (2011).
Li, et al., "Low-Level Vagosympathetic Stimulation. A Paradox and Potential New Modality for the Treatment of Focal Atrial Fibrillation," Circ Arrhythm Electrophysiol, Journal of American Heart Association, 2, pp. 645-651 (2009).
Li, et al., "Restoration of vagal tone by donepezil, on top of losartan treatment, markedly suppresses ventricular dysfunction and improves long-term survival in chronic heart failure rats," European Heart Journal, 32 (Abstract Supplement), pp. 642 (2011).
Li, et al., "Vagal nerve Stimulation Markedly Improves Long-Term Survival After Chronic Heart Failure in Rats," Circulation, Journal of the American Heart Association, 109, pp. 120-124 (2004).
Li et al., "Vagal Nerve Stimulation Markedly Improves Long-Term Survival After Chronic Heart Failure in Rats," Circulation: Journal of the American Heart Association, vol. 109, iss. 1, pp. 120-124 (Jan. 2004). Online publication date: Dec. 8, 2003. Available at: http://circ.ahajournals.org/cgi/pmidlookup?view=long&pmid=14662714.
Libby, et al., "Inflammation and Atherosclerosis," Circulation, Journal of the American Heart Association, 105, pp. 1135-1143 (2002).
Liu, et al., "Differing sympathetic and vagal effects on atrial fibrillation in dogs: role of refractoriness heterogeneity,"Am. J. Physiol. 273 (Heart Circ. Physiol. 42), pp. H805-H816 (1997).
Lo, et al., "Paradoxical long-term proarrhythmic effects after ablating the 'head station' ganglionated plexi of the vagal innervation to the heart," Heart Rhythm, vol. 10, No. 5, pp. 751-757 (May 2013).
Lohmeier, et al., "Prolonged Activation of the Barorelfex Products Sustained Hypotension," Hypertension, Journal of the American Heart Association, 43, pp. 306-311 (2004).
Lu, et al., "Vagal nerve stimulation protects cardiac injury by attenuating mitochondrial dysfunction in a murine burn injury model," J. Cell. Mol. Med., vol. 17, No. 5, pp. 664-671 (2013).
Ma, et al., "Analysis of afferent, central, and efferent components of the baroreceptor reflex in mice," Am J Physiol Regulatory Integration Comp Physiol, 283, pp. 1033-1040 (2002).
Maj, et al., "P5775: Autonomic imbalance and circulating androgens and estrogens in men with systolic heart failure," European Heart Journal, 32 (Abstract Supplement), pp. 1090 (2011).
Malkin, et al., "Life-saving or life-prolonging? Interpreting trial data and survival curves for patients with congestive heart failure," The European Journal of Heart Failure, 7, pp. 143-148 (2005).
Mann, "Chapter 12—Peripheral Nerves," The Nervous System in Action, michaeldmann.net/mann12.html, (Jul. 2011).
Mann, "Inflammatory Mediators and the Failing Heart. Past, Present, and the Foreseeable Future," Circ Res., 91, pp. 988-998 (2002).
Mann, "Stress-Activated Cytokines and the Heart: From Adaptation to Maladaptation," Annu. Rev. Physiol., 65, pp. 81-101 (2003).
Martin-Portugues, et al., "Histopathologic features of the vagus nerve after electrical stimulation in swine," Histol Histopathol, 20, pp. 851-856 (2005).
Martins, et al., "Distribution of Local Repolarization Changes Produced by Efferent Vagal Stimulation in the Canine Ventricles," JACC, vol. 2, No. 6, pp. 1191-1199 (Dec. 1983).
Massari, et al., "Neural control of left ventricular contractility in the dog heart: synaptic interactions of negative inotropic vagal preganglionic neurons in the nucleus ambiguus and tyrosine hydroxylase immunoreactive terminals," Brain Research, 802, pp. 205-220 (1998).
May, et al., "P564: Long-term prediction of all-cause mortality in diabetic autonomic neuropathy: simple function tests or 24-hour heart rate variability (HRV)?" European Heart Journal, 32 (Abstract Supplement, pp. 64 (2011).
Mei,et al., "The Composition of the Vagus Nerve of the Cat," Cell Tissue Res., 209, pp. 423-431 (1980).
Merrill, et al., "Electrical stimulation of excitable tissue: design of efficacious and safe protocols," Journal of Neuroscience Methods, 141, pp. 171-198 (2005).
Mortara, et al., "Arterial Baroreflex Modulation of Heart Rate in Chronic Heart Failure," Circulation, Journal of the American Heart Association, vol. 96, No. 10, pp. 3450-3458 (Nov. 18, 1997).
Murakawa, et al., "Effect of Cervical Vagal Nerve Stimulation on Defibrillation Energy," Jpn Heart J, 44, pp. 91-100 (Jan. 2003).
Naito, "Effects of zatebradine and propranolol on canine ischemia and reperfusion-induced arrhythmias," European Journal of Pharmacology, 388, pp. 171-176 (2000).
Nakajima, et al., "Autonomic Control of the Location and Rate of the Cardiac Pacemaker in the Sinoatrial Fat Pad of Parasympathetically Denervated Dog Hearts," Journal of Cardiovascular Electrophysiology, vol. 13, No. 9 pp. 896-901 (Sep. 2002).
Nearing, et al., "Crescendo in Depolarization and Repolarization Heterogeneity Heralds Development of Ventricular Tachycardia in Hospitalized Patients with Decompensated Heart Failure," Circu-

(56) References Cited

OTHER PUBLICATIONS lation Arrhythmia and Electrophysiology, Journal of the American Heart Association, 5, pp. 84-90 (2012).
Nihei, et al., "Decreased Vagal Control Over Heart Rate in Rats with Right-Sided Congestive Heart Failure—Downregulation of Neuronal Nitric Oxide Synthase," Circ J, 69, pp. 493-499 (2005).
Ninomiya, "Direct Evidence of Nonuniform Distribution of Vagal Effects on Dog Atria," Circulation Research, vol. XIX, pp. 576-583 (Sep. 1966).
Nolan, et al., "Prospective Study of Heart Rate Variability and Mortality in Chronic Heart Failure: Results of the United Kingdom Heart Failure Evaluation and Assessment of Risk Trial (UK-Heart)," Circulation, Journal of the American Heart Association, 98, pp. 1510-1516 (1998).
Ochoa, et al., "P2497: Effects of insulin resistance on resting heart rate, baroreflex sensitivity and indices of autonomic cardiovascular modulation in individuals with high blood pressure levels," European Heart Journal, 32 (Abstract Supplement, pp. 431-432 (2011).
Ogawa, et al., "Left Stellate Ganglion and Vagal Nerve Activity and Cardiac Arrhythmias in Ambulatory Dogs with Pacing-Induced Congestive Heart Failure," Journal of the American College of Cardiology, vol. 50, No. 4, pp. 335-444 (2007).
Okada, et al., "Cyclic Stretch Upregulates Production of Interleukin-8 and Monocyte Chemotactic and Activating Factor/Monocyte Chemoattractant Protein-1 in Human Endothelial Cells," Arterioscler Thromb Vasc Biol., 18, pp. 894-901 (1998).
Oliveira, et al., "Effects of vagal stimulation on induction and termination of atrial fibrillation in an in vivo rabbit heart model," Rev Port Cardiol, 29(03), pp. 375-389 (2010).
Olshansky, et al., "Parasympathetic Nervous System and Heart Failure: Pathophysiology and Potential Implications for Therapy," Circulation, Journal of the American Heart Association, 118, pp. 863-871 (2008).
Olshansky et al., "Parasympathetic Nervous System and Heart Failure: Pathophysiology and Potential Implications for Therapy," Circulation: Journal of the American Heart Association, vol. 118, iss. 8, pp. 863-871 (Aug. 2008).
Onkka, et al., "Sympathetic nerve fibers and ganglia in canine cervical vagus nerves: Localization and quantitation," Heart Rhythm, vol. 10, No. 4, pp. 585-591 (Apr. 2013).
Ordelman, et al., "Selectivity for Specific Cardiovascular Effects of Vagal Nerve Stimulation with a Multi-Contact Electrode Cuff," IEEE, pp. 1-6 (2011).
Packer, et al., "Effect of Carvedilol on Survival in Severe Chronic Heart Failure," The New England Journal of Medicine, vol. 344, No. 22, pp. 1651-1658 (May 31, 2001).
Pavlov, et al., "Central muscarinic cholinergic regulation of the systemic inflammatory response during endotoxemia," PNAS, vol. 103, No. 13, pp. 5219-5223 (Mar. 28, 2006).
Pavlov, et al., "Controlling inflammation: the cholinergic anti-inflammatory pathway," Biochemical Society Transactions, vol. 34, part 6, pp. 1037-1040 (2006).
Peckham, et al., "Chapter 18—Implantable Neural Stimulators," Neuromodulation, Academic Press (2009).
Pina, et al., "The Predictive Value of Biomarkers in Heart Failure," Medscape Education Cardiology, Available at http://www.medscape.org/viewarticle/765328 (CME Released: Jun. 15, 2012).
Pitzalis, et al., "Comparison Between Noninvasive Indices of Baroreceptor Sensitivity and the Phenylephrine Method in Post-Myocardial Infarction Patients," Circulation, Journal of the American Heart Association, 97, pp. 1362-1367 (1998).
Poole-Wilson, "Relation of Pathophysiologic Mechanisms to Outcome in Heart Failure," JACC, vol. 22, No. 4 (supplement A), pp. 22A-29A (Oct. 1993).
Pye, et al., "Study of serum C-reactive protein concentration in cardiac failure," Br Heart J, 63, pp. 228-230 (1990).
Rademacher, et al., "P5878: Multidimensional holter-based analysis of cardiac autonomic regulation predicts early AF recurrence after electrical cardioversion," European Heart Journal, 32 (Abstract Supplement), pp. 1116-1117 (2011).

Randall, et al., "Regional vagosympathetic control of the heart," American Journal of Physiology, vol. 227, No. 2, pp. 444-452 (1974).
Randall, et al., "Selective Vagal Innervation of the Heart," Annals of Clinical and Laboratory Science, vol. 16, No. 3, pp. 198-208 (1986).
Raymond, et al., "Elevated interleukin-6 levels in patients with asymptomatic left ventricular systolic dysfunction," American Heart Journal, vol. 141, No. 3, pp. 435-438 (Mar. 2001).
Rhee, et al., "Presentation Abstract—Effects of suprathreshold vagal stimulation on stellate ganglion nerve activity in ambulatory dogs," 33rd Annual Scientific Sessions, Heart Rhythm (2012).
Riccio, et al., "Interganglionic segregation of distinct vagal afferent fibre phenotypes in guinea-pig airways," Journal of Physiology, 495.2, pp. 521-530 (1996).
Riddle, et al., "Epidemiologic Relationships Between A1C and All-Cause Mortality During a Median 3.4-Year Follow-up of Glycemic Treatment in the ACCORD Trial," Diabetes Care, vol. 33, No. 5, pp. 983-990 (May 2010).
Ridker, C-Reactive Protein: A Simple Test to Help Predict Risk of Heart Attack and Stroke, Journal of the American Heart Association, 108, pp. e81-e85 (2003).
Ridker, et al., "Comparison of C-Reactive Protein and Low-Density Lipoprotein Cholesterol Levels in the Prediction of First cardiovascular Events," New England Journal of Medicine, vol. 347, No. 20, pp. 1557-1566 (Nov. 14, 2002).
Ridker, et al., "C-Reactive Protein and Other Markers of Inflammation in the Prediction of Cardiovascular Disease in Women," The New England Journal of Medicine, vol. 342, No. 12, pp. 836-841 (Mar. 23, 2000).
Ridker, et al., "Inflammation, Pravastatin, and the Risk of Coronary Events After Myocardial Infarction in Patients With Average Cholesterol Levels," Circulation, Journal of the American Heart Association, 98, pp. 839-844 (1998).
Roger, et al., "Heart Disease and Stroke Statistics—2011 Update: A Report from the American Heart Association," Circulation, Journal of the American Heart Association. Available at http://circ.ahajournals.org/content/123/4/e18 (2010).
Romanovsky, et al., "The vagus nerve in the thermoregulatory response to systemic inflammation," Am. J. Physiol., 273, pp. R407-R413 (1997).
Rossi, et al., "Epicardial ganglionated plexus stimulation decreases postoperative inflammatory response in humans," Heart Rhythm, vol. 9, No. 6, pp. 943-950 (Jun. 2012).
Rouse, et al., "The haemodynamic actions of ZENCA ZD7288, a novel sino-atrial node function modulator, in the exercising beagle: a comparison with zategradine and propranolol," Abstract, British Journal of Pharmacology, 113(3):1071-7 (1994).
Rozman, et al., "Heart function influenced by selective mid-cervical left vagus nerve stimulation in a human case study," Hypertension Research, 32, pp. 1041-1043 (2009).
Rutecki, "Anatomical, Physiological and Theoretical Basis for the Antiepileptic Effect of Vagus Nerve Stimulation," Epilepsia, 31 (suppl. 2), pp. S1-S6 (1990).
Sabbah, et al., "3722: Vagus nerve stimulation improves left ventricular function in heart failure: results of a 6 month investigation with a cross-over design in dogs with experimental heart failure," European Heart Journal, 32 (Abstract Supplement), pp. 642 (2011).
Sabbah, et al., "Baroreflex Activation Therapy for the Treatment of Heart Failure," Presentation available at http://www.cvrx.com/wp/wp-content/uploads/2012/04/Dr.-Sabbah-Slides.pdf (2012).
Sabbah, et al., "Chronic Electrical Stimulation of the Carotid Sinus Baroreflex Improves Left Ventricular Function and Promotes Reversal of Ventricular Remodeling in Dogs with Advanced Heart Failure," Circulation Heart Failure, Journal of the American Heart Association, 4, pp. 65-70 (2011).
Sabbah, et al., "Vagus nerve stimulation in experimental heart failure," Heart Fail Rev, 16, pp. 171-178 (2011).
Sabbah et al., "Vagus nerve stimulation in experimental heart failure," Heart Failure Reviews, vol. 16, No. 2, pp. 171-178 (Mar. 2011). Online Publication Date: Dec. 3, 2010.

(56) References Cited

OTHER PUBLICATIONS

Samara, et al., "The Effects of Cardiac Resyhchronization Therapy on Chronotropic Incompetence in Patients Intolerant of Beta Antagonist Therapy," Journal of Cardiac Failure, vol. 17, No. 8S, pp. S-54-S55 (Aug. 2011).
Sanner, et al., "P4743: Prediction of cardiovascular risk from nocturnal pulse wave signal using the autonomic state indicator (ASI) technology," European Heart Journal, 32 (Abstract Supplement), pp. 839 (2011).
Sato, et al., "Serial Circulating Concentrations of C-Reactive Protein, Interleukin (IL)-4, and IL-6 in Patients with Acute Left Heart Decompensation," Clin. Cardiol. 22, pp. 811-813 (1999).
Schauerte, "Time for Change: Cardiac neurophysiology meets cardiac electrophysiology," Editorial Commentary, Heart Rhythm Society (2013).
Schiereck, et al., "AV blocking due to asynchronous vagal stimulation in rats," Am J Physiol Heart Circ Physiol, 278, pp. H67-H73 (2000).
Schocken, et al., "Prevalence and Mortality Rate of Congestive Heart Failure in the United States," JACC, vol. 20, No. 2, pp. 301-306 (Aug. 1992).
Schwartz, "Vagal Stimulation for Heart Diseases: From Animals to Men," Circulation Journal, vol. 75, pp. 20-27 (Jan. 2011).
Schwartz, "Vagal stimulation for heart failure," Current Opinion in Cardiology, 26, pp. 51-54 (2011).
Schwartz, "Vagal stimulation for the treatment of heart failure: a translational success story," Heart, vol. 98, No. 23, pp. 1687-1690 (2012).
Schwartz, et al. Vagal stimulation for heart failure: Background and first in-man study, Heart Rhythm, 6, 11 suppl., pp. S76-S81 (Nov. 2009).
Schwartz, et al., "Autonomic mechanisms and sudden death. New insights from analysis of baroreceptor reflexes in conscious dogs with and without myocardial infarction," Circulation, Journal of the American Heart Association, 78, pp. 969-979 (1988).
Schwartz, et al., "Effects of Unilateral Cardiac Sympathetic Denervation on the Ventricular Fibrillation Threshold," The American Journal of Cardiology, vol. 37, pp. 1034-1040 (Jun. 1976).
Schwartz, et al., "Long term vagal stimulation in patients with advanced heart failure. First experience in man," European Journal of Heart Failure, 10, pp. 884-891 (2008).
Schwartz, et al., "Sympathetic-parasympathetic interaction in health and disease: abnormalities and relevance in heart failure," Heart Fail Rev, 16, pp. 101-107 (2011).
Seta, et al., "Basic Mechanisms in Heart Failure: The Cytokine Hypotehsis," Journal of Cardiac Failure, vol. 2, No. 3, pp. 243-249 (1996).
Sha, et al., "Low-Level Right Vagal Stimulation: Anticholinergic and Antiadrenergic Effects," J Cardiovasc Electrophysiol, pp. 1-7 (Feb. 2011).
Shamoon, et al., The Diabetes Control and Complications Trial Research Group, "The effect of intensive treatment of diabetes on the development and progression of long-term complications in insulin-dependent diabetes mellitus," The New England Journal of Medicine, vol. 329, No. 14, pp. 977-986 (Sep. 30, 1993).
Shannon, "A Model of Safe Levels for Electrical Stimulation," IEEE Transactions on Biomedical Engineering, vol. 39, No. 4, pp. 424-426 (Apr. 1992).
Shen, et al., "Continuous Low-Level Vagus Nerve Stimulation Reduces Stellate Ganglion Nerve Activity and Paroxysmal Atrial Tachyarrhythmias in Ambulatory Canines," Circulation, Journal of the American Heart Association, 123, pp. 2204-2212 (2011).
Shen, etl al., "Low-level vagus nerve stimulation upregulates small conductance calcium-activated potassium channels in the stellate ganglion," Heart Rhythm, vol. 10, No. 6, pp. 910-915 (2013).
Shinohara, et al., "Heart Failure Decreases Nerve Activity in the Right Atrial Ganglionated Plexus," J Cardiovasc Electrophysiol, pp. 1-9 (2011).
Shioi, et al., "Increased Expression of Interleukin-1B and Monocyte Chemotactic and Activating Factor/Monocyte Chemoattractant Protein-1 in the Hypertrophied and Failing Heart with Pressure Overload," Circ Res., 81, pp. 664-671 (1997).
Singal, et al., "The role of oxidative stress in the genesis of heart disease," Cardiovascular Research, 40, pp. 426-432 (1998).
Spuck, et al., "Right-sided vagus nerve stimulation in humans: An effective therapy?" Epilepsy Research, pp. 1-3 (2008).
Stein, et al., "A Simple Method to Identify Sleep Apnea Using Holter Recordings," J Cardiovasc Electrophysiol, vol. 14, pp. 467-473 (May 2003).
Stein, et al., "Feasibility of Using Mobile Cardiac Outpatient Telemetry (MCOT) to Identify Severe Sleep Disorders" (2009).
Stieber, et al., "Bradycardic and proarrhythmic properties of sinus node inhibitors," Abstract, Molecular Pharmacology, 69(4):1328-37 (2006).
Taylor, et al., "The unequal influences of the left and right vagi on the control of the heart and pulmonary artery in the rattlesnake, *Crotalus durissus*," The Journal of Experimental Biology, 212, pp. 145-151 (2009).
Thayer, et al., "The role of vagal function in the risk for cardiovascular disease and mortality," Biological Psychology, 74, pp. 224-242 (2007).
Thollon, et al., "Electrophysiological effects of S 16257, a novel sino-atrial node modulator, on rabbit and guinea-pig cardiac preparations: comparison with UL-FS 49," Abstract, British Journal of Pharmacology, 112(1):37-42 (1994).
Tosato, et al., "Quasi-trapezoidal pulses to selectively block the activation of intrinsic laryngeal muscles during vagal nerve stimulation," J. Neural Eng., 4, pp. 205-212 (2007).
Tsutsumi, et al., "Modulation of the myocardial redox state by vagal nerve stimulation after experimental myocardial infarction," Cardiovascular Research, 77, pp. 713-721 (2008).
Tyler, et al., "Chapter 17—Electrodes for the Neural Interface," Neuromodulation, Academic Press (2009).
Ulphani, et al., "Quantitative analysis of parasympathetic innervation of the porcine heart," Heart Rhythm, 7, pp. 1113-1119 (2010).
Uthman, et al., "Effectiveness of vagus nerve stimulation in epilepsy patients. A 12-year observation," Neurology, 63, pp. 1124-1126 (2004).
Van Stee, "Autonomic Innervation of the Heart," Environmental Health Perspectives, vol. 26, pp. 151-158 (1978).
Vanoli, et al., "Vagal stimulation and prevention of sudden death in conscious dogs with a healed myocardial infarction," Circulation Research, Journal of the American Heart Association, 68, pp. 1471-1481 (1991).
Vasan,. et al., "Inflammatory Markers and Risk of Heart Failure in Elderly Subjects Without Prior Myocardial Infarction," Circulation, Journal of the American Heart Association, 107, pp. 1486-1491 (2003).
Vassalle, et al., "An Analysis of Arrhythmias Induced by Ouabain in Intact Dogs," Circulation Research, Journal of the American Heart Association, 13, pp. 132-148 (1963).
Velagaleti, et al., "Long-Term Trends in the Incidence of heart Failure After Myocardial Infarction," 118, pp. 2057-2062 (2008).
Verrier, et al., "Microvolt T-Wave Alternans," Journal of the American College of Cardiology, vol. 58, No. 13, pp. 1309-1324 (2011).
Vimercati, et al., "Acute vagal stimulation attenuates cardiac metabolic response to B-adrenergic stress," The Journal of Physiology,vol. 500, No. 23, pp. 6065-6074 (2012).
Wang, et al., "Nicotinic acetylcholine receptor 7 subunit is an essential regulator of inflammation," Nature, vol. 421, pp. 384-388 (Jan. 23, 2003).
Wang, et al., "Synaptic and Neurotransmitter Activation of Cardiac Vagal Neurons in the Nucleus Ambiguus," Annals New York Academy of Sciences, pp. 237-246 (2001).
Waninger, et al., "Characterization of Atrioventricular Nodal Response to Electrical Left Vagal Stimulation," Annals of Biomedical Engineering, vol. 27, pp. 758-762 (1999).
Wann, "Behavioural signs of depression and apoptosis in the limbic system following myocardial infarction: effects of sertraline," Journal of Psychopharmacology, 23(4), pp. 451-459 (2009).

(56) References Cited

OTHER PUBLICATIONS

Wann, et al., "Vulnerability for apoptosis in the limbic system after myocardial infarction in rats: a possible model for human postinfarct major depression," J Psychiatry Neurosci, 32(1):11-6, pp. 11-16 (2007).
Watkins, et al., "Cytokine-to-Brain Communication: A Review & Analysis of Alternative Mechanisms," Life Sciences, vol. 57, No. 11, pp. 1011-1026 (1995).
Whyte, et al., "Reactive oxygen species modulate neuronal excitability in rat intrinsic cardiac ganglia," Auton Neurosci, 150(1-2), pp. 45-52 (Oct. 5, 2009).
Wieland, et al., "Bradycardic and proarrhythmic properties of sinus node inhibitors," Abstract, Molecular Pharmacology, 69(4):1328-37 (2006).
Yang, et al., "Sustained increases in heart rate induced by time repetition of vagal stimulation in dogs," Am. J. Physiol., 249, pp. H703-H709 (1985).
Yin, et al., "Independent prognostic value of elevated high-sensitivity C-reactive protein in chronic heart failure," American Heart Journal, vol. 147, No. 5, pp. 931-938 (2004).
Yndestad, et al., "Systemic inflammation in heart failure—The whys and wherefores," Heart Fail Rev, 11, pp. 83-92 (2006).
Yoo, et al., "High-resolution measurement of electrically-evoked vagus nerve activity in the anesthetized dog," J. Neural Eng., 10, pp. 1-9 (2013).
Yoo, et al., "Selective Control of Physiological Responses by Temporally-Patterned Electrical Stimulation of the Canine Vagus Nerve," 33rd Annual International Conference of the IEEE EMBS (2011).
Yu, et al., "Interactions between atrial electrical remodeling and autonomic remodeling: How to break the vicious cycle," Heart Rhythm, 9, pp. 804-809 (2012).
Yu, et al., "Low-level transcutaneous electrical stimulation of the auricular branch of the vagus nerve: A noninvasive approach to treat the initial phase of atrial fibrillation," Heart Rhythm, 10, pp. 428-435 (2013).

Yuan, et al., "Gross and Microscopic Anatomy of the Canine Intrinsic Cardiac Nervous System," The Anatomical Record, 239, pp. 75-87 (1994).
Yusuf, et al., "Changes in Hypertension Treatment and in Congestive Heart Failure Mortality in the United States," Hypertension, Journal of the American Heart Association, 13:174-1179 (1989).
Zhang, et al., "Arrhythimias and vagus nerve stimulation," Heart Fail Rev, 16, pp. 147-161 (2011).
Zhang, et al., "Chronic Vagus Nerve Stimulation Improves Autonomic Control and Attenuates Systemic Inflammation and Heart Failure Progression in a Canine High-Rate Pacing Model," Journal of the American Heart Association, Circ Heart Fail, 2, pp. 692-699 (2009).
Zhang, et al., "Involvement of activated astrocyte and microglia of locus coeruleus in cardiac pain processing after acute cardiac injury," Neurol Res, 31, pp. 432-438 (2009).
Zhang, et al., "Relationship between right cervical vagus nerve stimulation and atrial fibrillation inducibility: Therapeutic intensities do not increase arrhythmogenesis," Heart Rhythm, 6, pp. 244-250 (2009).
Zhang, et al., "Therapeutic Effects of Selective Atrioventricular Node Vagal Stimulation in Atrial Fibrillation and Heart Failure," Journal of Cardiovascular Electrophysiology, vol. 24, Issue 1, pp. 86-91 (2012).
Zheng, et al., "Vagal stimulation markedly suppresses arrhythmias in conscioius rats with chronic heart failure after myocardial infarction," Proceedings of the 2005 IEEE (2005).
Zipes, et al., "Effects of selective vagal and stellate ganglion stimulation on atrial refractoriness," Cardiovascular Research, 8, pp. 647-655 (1974).
Zucker, et al., "Chronic Baroreceptor Activation Enhances Survival in Dogs with Pacing-Induced Heart Failure," Journal of the American Heart Association, Hypertension (2007).
PCT Application No. PCT/US2014/024827, Search Report and Written Opinion dated Nov. 11, 2014, 18 pages.
PCT Application No. PCT/US2015/020116, Search Report and Written Opinion dated Jul. 6, 2015, 12 pages.
PCT Application No. PCT/US2014/024827, International Preliminary Report on Patentability dated Sep. 15, 2015, 11 pages.

* cited by examiner

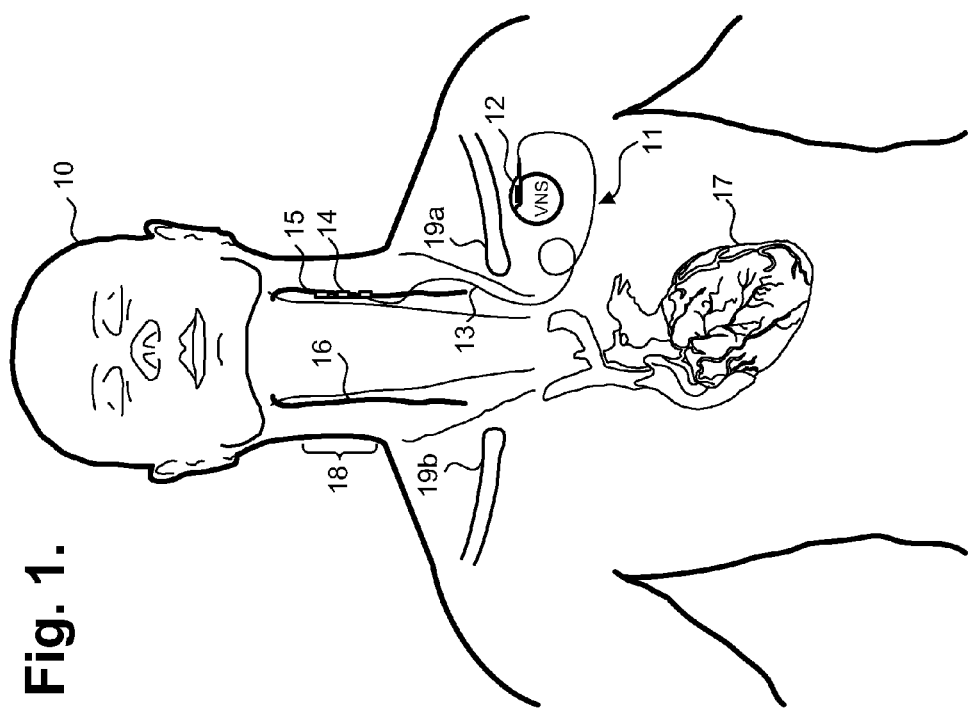
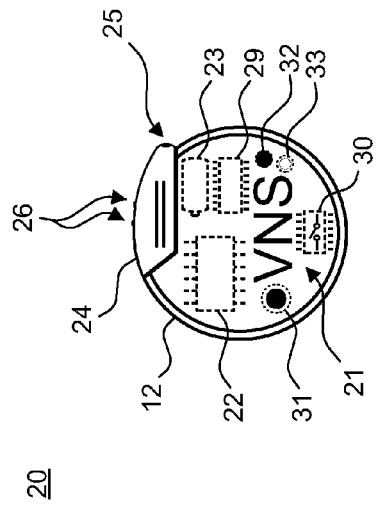
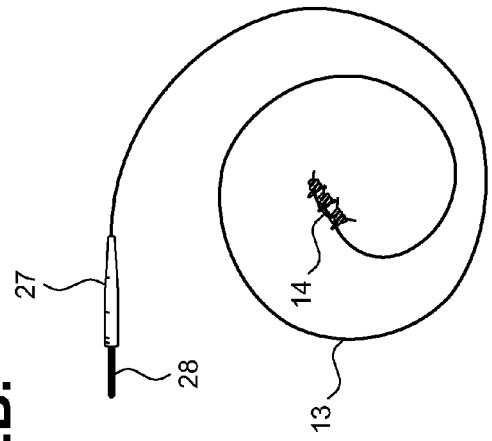
Fig. 1.
Fig. 2A.
Fig. 2B.

70

Fig. 5 (con'd).
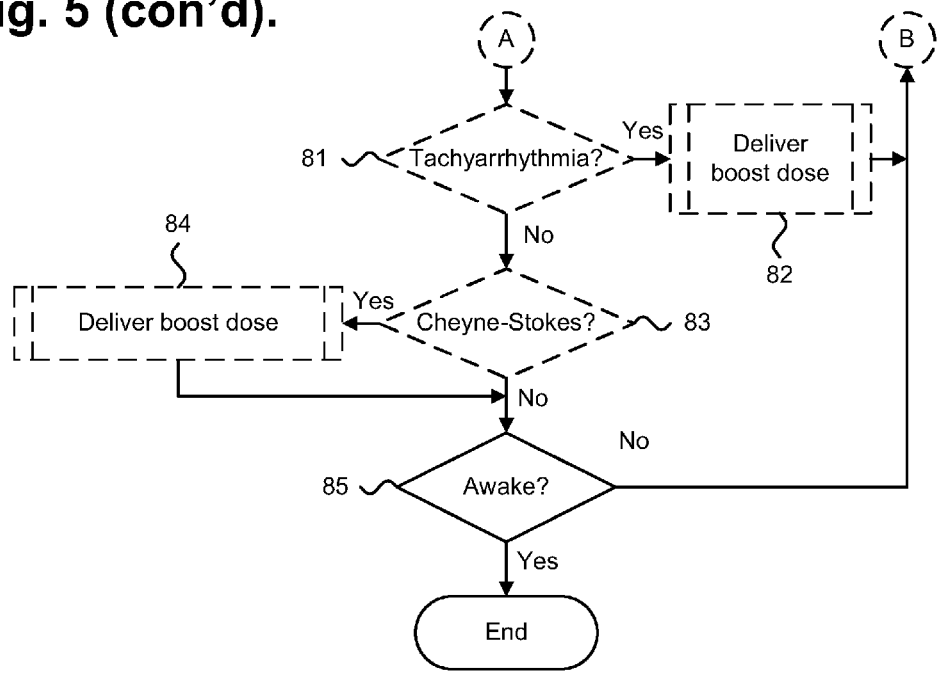
Fig. 6.
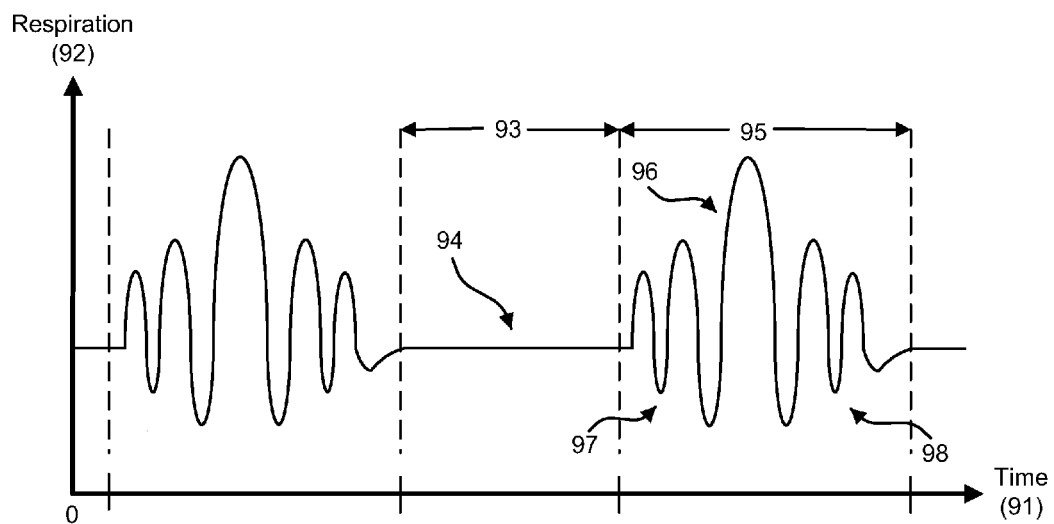

IMPLANTABLE NEUROSTIMULATOR-IMPLEMENTED METHOD FOR MANAGING TACHYARRHYTHMIC RISK DURING SLEEP THROUGH VAGUS NERVE STIMULATION

FIELD

This application relates in general to chronic cardiac dysfunction therapy and, in particular, to an implantable neurostimulator-implemented method for managing tachyarrhythmic risk during sleep through vagus nerve stimulation.

BACKGROUND

Congestive heart failure (CHF) is a chronic medical condition in which the heart is unable to pump sufficient blood to meet the body's needs. If left untreated, CHF can lead to cardiac arrhythmogenesis, progressively worsening cardiac function and eventually patient death. CHF patients are at increased risk of tachyarrhythmias, such as atrial fibrillation (AF), ventricular tachyarrhythmias (ventricular tachycardia (VT) and ventricular fibrillation (VF)), and atrial flutter, particularly when the underlying morbidity is a form of coronary artery disease, cardiomyopathy, mitral valve prolapse, or other valvular heart disease.

Additionally, around one half of the patients suffering from CHF or stroke develop a type of central sleep apnea (CSA), known as Cheyne-Stokes respiration, which is a breathing disorder that can occur during sleep or wakefulness during which the patient alternates between episodes of apnea and rapid breathing. In contrast to obstructive sleep apnea (OSA), which is caused by a physical blockage of the airway, CSA is due to an imbalance of respiratory control by the brain, where the brain fails to transmit signals to breathing muscles, thereby causing breathing to temporarily stop. Cessation of breathing in CSA causes hypoxaemia as the percentage of oxygen in the blood drops below normal levels and hypercapnia as the concentration of carbon dioxide in the blood rises to higher than normal levels. In CSA, central respiratory drive is absent and the brain fails to respond to the changing levels of these respiratory gases, resulting in an elevated heart rate. A severe drop in blood oxygen level due to CSA can cause angina, trigger arrhythmias or even myocardial infarction.

Even without developing OSA, CHF patients face increased cardiac risks during sleep that stem from a circadian rhythm-driven interplay of the sympathetic and parasympathetic nervous systems, particularly during non-rapid eye movement (NREM) sleep, which occupies about 75% of a night's sleep. During NREM sleep, sympathetic activation is withdrawn, while parasympathetic neural activity predominates and causes natural decreases in heart rate, blood pressure, cardiac output, arterial baroreceptor set point, and systemic vascular resistance. As a result, during NREM sleep, all persons may experience sinus bradycardia or sinus pauses lasting up to two seconds, and transitory atrioventricular blockages. While these conditions are benign in healthy persons, the risk of developing pathological bradyarrhythmias during NREM sleep can be of particular concern in CHF patients. Moreover, the threat of bradyarrhythmias during sleep is exacerbated in CHF patients suffering from CSA, who additionally experience an increased incidence of nocturnal AF and VT and multiple tachyarrhythmic events. Further, sleep apneic induction of hypoxia can lead to bradyarrhythmia with profound effect, as sequela hyperventilation can potentially trigger tachyarrhythmia, which can degrade into VF and eventual patient death.

CSA can exacerbate CHF through hypoxaemic-increased heart rate and heightened arrhythmogenic risk. CHF, as well as other forms of chronic cardiac dysfunction (CCD), are generally accompanied by an autonomic imbalance of the sympathetic and parasympathetic nervous systems and pathologically characterized by an elevated neuroexitatory state and impaired arterial and cardiopulmonary baroreflex function with reduced vagal activity. CHF triggers compensatory activations of the sympathoadrenal (sympathetic) nervous system and the renin-angiotensin-aldosterone hormonal system, which initially helps to compensate for deteriorating heart-pumping function, yet, over time, can promote progressive left ventricular dysfunction and deleterious cardiac remodeling. Sympathoadrenal activation, particularly when co-occurring with a sleep apneic episode, increases the risk and severity of tachyarrhythmias due to neuronal action of the sympathetic nerve fibers in, on, or around the heart and through the release of epinephrine (adrenaline), which can worsen an already-elevated heart rate.

Therapeutic electrical stimulation of neural structures that directly address the cardiac autonomic nervous system imbalance and dysregulation underlying CCD through high intensity neural stimulation has been proposed. In one form, the cervical vagus nerve is stimulated to directly modulate cardiovascular regulatory function. Currently, vagus nerve stimulation (VNS) is only approved for the clinical treatment of drug-refractory epilepsy and depression, but has been proposed for therapeutic treatment of CHF. For instance, VNS has been demonstrated in canine studies as efficacious in simulated treatment of AF and heart failure, such as described in Zhang et al., "Therapeutic Effects of Selective Atrioventricular Node Vagal Stimulation in Atrial Fibrillation and Heart Failure," J. Cardiovasc. Electrophysiol., Vol. 24, pp. 86-91 (January 2013), the disclosure of which is incorporated by reference.

Conventional VNS for cardiac therapy generally targets the efferent nerves of the parasympathetic nervous system, such as described in Sabbah et al., "Vagus Nerve Stimulation in Experimental Heart Failure," Heart Fail. Rev., 16:171-178 (2011), the disclosure of which is incorporated by reference. Sabbah discusses canine studies using a VNS system manufactured by BioControl Medical Ltd., Yehud, Israel, that includes an electrical pulse generator, right ventricular endocardial sensing lead, and right vagus nerve cuff stimulation lead. The sensing lead enables closed loop synchronization to the cardiac cycle; stimulation is delivered only when heart rate increases beyond a preset threshold. An asymmetric tri-polar nerve cuff electrode provides cathodic induction of action potentials while simultaneously applying asymmetric anodal blocks that lead to preferential activation of vagal efferent fibers. Stimulation is provided at an intensity and impulse rate intended to measurably reduce basal heart rate by ten percent by preferential stimulation of efferent vagus nerve fibers leading to the heart while blocking afferent neural impulses to the brain. The degree of therapeutic effect on parasympathetic activation occurs through incidental recruitment of afferent parasympathetic nerve fibers in the vagus, as well as through recruitment of efferent fibers.

Other uses of electrical nerve stimulation for therapeutic treatment of cardiac and physiological conditions are described. For instance, U.S. Pat. No. 8,219,188, issued Jul. 10, 2012 to Craig discloses synchronization of vagus nerve stimulation with a physiological cycle, such as the cardiac or respiratory cycle, of a patient. Electrical stimulation is applied to the vagus nerve at a selected point in the physiological cycle correlated with increased afferent conduction, such as a point from about 10 msec to about 800 msec after an R-wave of the patient's ECG, optionally during inspiration by the patient; to increase heart rate variability, such as a point from about 10 msec to about 800 msec after an R-wave of the patient's ECG, optionally during expiration by the patient; not correlated with increased efferent conduction on the vagus nerve; to generate efferent electrical activity on the vagus nerve; or upon the detection of a symptom of a medical condition. In a further embodiment, conventional VNS is applied to the vagus nerve along with microburst electrical signals, which is a portion of a therapeutic electrical signal having a limited plurality of pulses, separated from one another by interpulse intervals, and a limited burst duration, separated from one another by interburst periods. Stimulation may be applied to generate efferent electrical activity on the nerve in a direction away from the central nervous system; through a "blocking" type of electrical signal, such that both afferent and efferent electrical activity on the nerve is prevented from traveling further; or wherein afferent fibers are stimulated while efferent fibers are not stimulated or are blocked, and vice versa. By applying a series of microbursts to the vagus nerve, enhanced vagal evoked potentials (eVEP) are produced in therapeutically significant areas of the brain, in contrast to conventional VNS alone, which fails to produce eVEP.

U.S. Pat. No. 6,600,954, issued Jul. 29, 2003 to Cohen et al. discloses a method and apparatus for selective control of nerve fiber activations for reducing pain sensations in the legs and arms. An electrode device is applied to a nerve bundle capable of generating, upon activation, unidirectional action potentials that propagate through both small diameter and large diameter sensory fibers in the nerve bundle, and away from the central nervous system.

U.S. Pat. No. 6,684,105, issued Jan. 27, 2004 to Cohen et al. discloses an apparatus for treatment of disorders by unidirectional nerve stimulation. An apparatus for treating a specific condition includes a set of one or more electrode devices that are applied to selected sites of the central or peripheral nervous system of the patient. For some applications, a signal is applied to a nerve, such as the vagus nerve, to stimulate efferent fibers and treat motility disorders, or to a portion of the vagus nerve innervating the stomach to produce a sensation of satiety or hunger. For other applications, a signal is applied to the vagus nerve to modulate electrical activity in the brain and rouse a comatose patient, or to treat epilepsy and involuntary movement disorders.

U.S. Pat. No. 7,123,961, issued Oct. 17, 2006 to Kroll et al. discloses stimulation of autonomic nerves. An autonomic nerve is stimulated to affect cardiac function using a stimulation device in electrical communication with the heart by way of three leads suitable for delivering multi-chamber stimulation and shock therapy. For arrhythmia detection, the device utilizes atrial and ventricular sensing circuits to sense cardiac signals to determine whether a rhythm is physiologic or pathologic. The timing intervals between sensed events are classified by comparing them to a predefined rate zone limit and other characteristics to determine the type of remedial therapy needed, which includes bradycardia pacing, anti-tachycardia pacing, cardioversion shocks (synchronized with an R-wave), or defibrillation shocks (delivered asynchronously).

U.S. Pat. No. 7,225,017, issued May 29, 2007 to Shelchuk discloses terminating ventricular tachycardia in connection with any stimulation device that is configured or configurable to stimulate nerves, or stimulate and shock a patient's heart. Parasympathetic stimulation is used to augment anti-tachycardia pacing, cardioversion, or defibrillation therapy. To sense atrial or ventricular cardiac signals and provide chamber pacing therapy, particularly on the left side of the heart, the stimulation device is coupled to a lead designed for placement in the coronary sinus or its tributary veins. Cardioversion stimulation is delivered to a parasympathetic pathway upon detecting a ventricular tachycardia. A stimulation pulse is delivered via the lead to electrodes positioned proximate to the parasympathetic pathway according to stimulation pulse parameters based at least in part on the probability of reinitiation of an arrhythmia.

U.S. Pat. No. 7,277,761, issued Oct. 2, 2007 to Shelchuk discloses vagal stimulation for improving cardiac function in heart failure patients. An autonomic nerve is stimulated to affect cardiac function by way of three leads suitable for delivering multi-chamber endocardial stimulation and shock therapy. When the stimulation device is intended to operate as an implantable cardioverter-defibrillator (ICD), the device detects the occurrence of an arrhythmia, and applies a therapy to the heart aimed at terminating the detected arrhythmia. Defibrillation shocks are generally of moderate to high energy level, delivered asynchronously, and pertaining exclusively to the treatment of fibrillation.

U.S. Pat. No. 7,295,881, issued Nov. 13, 2007 to Cohen et al. discloses nerve branch-specific action potential activation, inhibition and monitoring. Two preferably unidirectional electrode configurations flank a nerve junction from which a preselected nerve branch issues with respect to the brain. Selective nerve branch stimulation can be used in conjunction with nerve-branch specific stimulation to achieve selective stimulation of a specific range of fiber diameters, substantially restricted to a preselected nerve branch, including heart rate control, where activating only the vagal B nerve fibers in the heart, and not vagal A nerve fibers that innervate other muscles, can be desirous.

U.S. Pat. No. 7,778,703, issued Aug. 17, 2010 to Gross et al. discloses selective nerve fiber stimulation for treating heart conditions. An electrode device is coupled to a vagus nerve and a control unit applies stimulating and inhibiting currents to the vagus nerve, which are capable of respectively inducing action potentials in a therapeutic direction in first and second sets of nerve fibers in the vagus nerve and inhibiting action potentials in the therapeutic direction in the second set of nerve fibers only. The nerve fibers in the second set have larger diameters than the first set's nerve fibers. Typically, the system is configured to treat heart failure or heart arrhythmia, such as AF or tachycardia by slowing or stabilizing the heart rate, or reducing cardiac contractility.

U.S. Pat. No. 7,813,805, issued Oct. 12, 2010 to Farazi and U.S. Pat. No. 7,869,869, issued Jan. 11, 2011 to Farazi both disclose subcardiac threshold vagus nerve stimulation. A vagus nerve stimulator is configured to generate electrical pulses below a cardiac threshold, which are transmitted to a vagus nerve, so as to inhibit or reduce injury resulting from ischemia. For arrhythmia detection, a heart stimulator utilizes atrial and ventricular sensing circuits to sense cardiac signals to determine whether a rhythm is physiologic or pathologic. In low-energy cardioversion, an ICD device typically delivers a cardioversion stimulus synchronously with a QRS complex. If anti-tachycardia pacing or cardioversion fails to terminate a tachycardia, after a programmed time interval or if the tachycardia accelerates, the ICD device initiates defibrillation.

U.S. Patent App. Pub. No. 2010/0331908, filed Sep. 10, 2010 by Farazi discloses subcardiac threshold vagus nerve stimulation in which a vagal nerve stimulator generates electrical pulses below a cardiac threshold of the heart for treating an ischemia of the heart, or for reducing a defibrillation threshold of the heart. The cardiac threshold is a threshold for energy delivered to the heart above which there is a slowing of the heart rate or the conduction velocity. In operation, the vagal nerve stimulator generates the electrical pulses below the cardiac threshold, that is, subcardiac threshold electrical pulses, such that the beat rate of the heart is not affected. Although the function of the vagal nerve stimulator is to treat an ischemia, or to reduce a defibrillation threshold of the heart, in other embodiments, the vagal nerve stimulator may function to treat heart failure, reduce an inflammatory response during a medical procedure, stimulate the release of insulin for treating diabetes, suppress insulin resistance for treating diabetes, or treat an infarction of the heart.

U.S. Pat. No. 7,634,317, issued Dec. 15, 2009, to Ben-David et al. discloses techniques for applying, calibrating and controlling nerve fiber stimulation, which includes a vagal stimulation system comprising a multipolar electrode device that is applied to a portion of a vagus nerve (a left vagus nerve and/or right vagus nerve), which innervates a heart of a subject. Alternatively, the electrode device is applied to an epicardial fat pad, a pulmonary vein, a carotid artery, a carotid sinus, a coronary sinus, a vena cava vein, a right ventricle, or a jugular vein. The system is utilized for treating a heart condition such as heart failure and/or cardiac arrhythmia; the vagal stimulation system further comprises an implantable or external control unit, which typically communicates with electrode device over a set of leads. Typically, the control unit drives the electrode device to (i) apply signals to induce the propagation of efferent nerve impulses towards heart, and (ii) suppress artificially-induced afferent nerve impulses towards a brain of the subject, to minimize unintended side effects of the signal application; the efferent nerve pulses in vagus nerve are typically induced by the electrode device to regulate the heart rate of the subject.

Finally, U.S. Pat. No. 7,885,709, issued Feb. 8, 2011 to Ben-David discloses nerve stimulation for treating disorders. An electrode device stimulates the vagus nerve, so as to modify heart rate variability, or to reduce heart rate, by suppressing the adrenergic (sympathetic) system. Typically, the system is configured to treat heart failure or heart arrhythmia. Therapeutic effects of reduction in heart rate variability include the narrowing of the heart rate range, thereby eliminating very slow heart rates and very fast heart rates. For this therapeutic application, the control unit is typically configured to reduce low-frequency heart rate variability, and to adjust the level of stimulation applied based on the circadian and activity cycles of the subject. Therapeutic effects also include maximizing the mechanical efficiency of the heart by maintaining relatively constant ventricular filling times and pressures.

Notwithstanding, a need remains for an approach to ameliorate cardiac arrhythmogenic risk in a patient suffering from some form of CCD during sleep or due to a sleep-related disorder, such as CSA.

SUMMARY

CHF causes compensatory activation of the sympathetic nervous system and decreased parasympathetic central outflow, which can have a long-term negative effect on cardiac performance. A patient suffering from CHF, as well as other forms of CCD, is at increased risk of cardiac arrhythmogenesis during sleep, particularly if experiencing CSA as a co-morbidity. Low intensity peripheral neurostimulation therapies that target the imbalance of the autonomic nervous system have been shown to improve clinical outcomes. Thus, bi-directional autonomic regulation therapy is delivered to the cervical vagus nerve at an intensity that is insufficient to elicit pathological or acute physiological side effects and without the requirement of an enabling physiological feature or triggering physiological marker. The patient's physiology is monitored to identify periods of sleep. In one embodiment, upon sensing a condition indicative of tachyarrhythmia following a period of bradycardia, as naturally occurs during sleep, an enhanced "boost" dose of bi-directional neural stimulation intended to "break" the tachyarrhythmic condition is delivered. In a further embodiment, the boost dose is delivered upon sensing a physiological pattern indicative of Cheyne-Stokes respiration.

One embodiment provides an implantable neurostimulator-implemented method for managing tachyarrhythmic risk during sleep through vagus nerve stimulation. An implantable neurostimulator, including a pulse generator configured to deliver electrical therapeutic stimulation in a manner that results in creation and propagation (simultaneously in both afferent and efferent directions) of action potentials within neuronal fibers of a patient's cervical vagus nerve, is provided. Operating modes of the pulse generator are stored in a recordable memory. A maintenance dose of the electrical therapeutic stimulation is parametrically defined and is tuned to restore cardiac autonomic balance through continuously-cycling, intermittent and periodic electrical pulses at an intensity that is insufficient to elicit pathological or acute physiological side effects and without requirement of an enabling physiological feature or triggering physiological marker. A boost dose of the electrical therapeutic stimulation is parametrically defined and is tuned to prevent initiation of or disrupt tachyarrhythmia through periodic electrical pulses delivered at higher intensity than the maintenance dose. The maintenance dose is therapeutically delivered to the vagus nerve independent of cardiac cycle via a pulse generator included in the implantable neurostimulator through at least a pair of helical electrodes electrically coupled to the pulse generator via a nerve stimulation therapy lead. The patient's physiological state while asleep is monitored via at least one sensor included in the implantable neurostimulator. Upon sensing a condition indicative of naturally-occurring bradycardia followed by a condition indicative of potential tachyarrhythmia, the boost dose is delivered to the vagus nerve via the pulse generator through the pair of helical electrodes.

A further embodiment provides an implantable neurostimulator-implemented method for managing tachyarrhythmic risk accompanying central sleep apnea through vagus nerve stimulation. An implantable neurostimulator, including a pulse generator configured to deliver electrical therapeutic stimulation in a manner that results in creation and propagation (simultaneously in both afferent and efferent directions) of action potentials within neuronal fibers including a patient's cervical vagus nerve, is provided. Operating modes of the pulse generator are stored in a recordable memory. A maintenance dose of the electrical therapeutic stimulation is parametrically defined and is tuned to restore cardiac autonomic balance through continuously-cycling, intermittent and periodic electrical pulses at an intensity that is insufficient to elicit pathological or acute physiological side effects and without requirement of an enabling physiological feature or triggering physiological marker. A boost dose of the electrical therapeutic stimulation is parametrically defined and is tuned to prevent initiation of or disrupt tachyarrhythmia through periodic electrical pulses delivered at higher intensity than the maintenance dose. The maintenance dose is therapeutically delivered to the vagus nerve independent of cardiac cycle via a pulse generator included in the implantable neurostimulator through at least a pair of helical electrodes electrically coupled to the pulse generator via a nerve stimulation therapy lead. The patient's physiological state is monitored via at least one sensor included in the implantable neurostimulator. Upon sensing a pattern indicative of Cheyne-Stokes respiration, the boost dose is delivered to the vagus nerve via the pulse generator through the pair of helical electrodes.

By improving autonomic balance and cardiovascular regulatory function, therapeutic VNS operates acutely to decrease heart rate, reflexively increase heart rate variability and coronary flow, reduce cardiac workload through vasodilation, and improve left ventricular relaxation without aggravating comorbid tachyarrhythmia or other cardiac arrhythmic conditions. Over the long term, low dosage VNS provides the chronic benefits of decreased negative cytokine production, increased baroreflex sensitivity, increased respiratory gas exchange efficiency, favorable gene expression, renin-angiotensin-aldosterone system down-regulation, and anti-arrhythmic, anti-apoptotic, and ectopy-reducing anti-inflammatory effects.

Still other embodiments of the present invention will become readily apparent to those skilled in the art from the following detailed description, wherein are described embodiments by way of illustrating the best mode contemplated for carrying out the invention. As will be realized, the invention is capable of other and different embodiments and its several details are capable of modifications in various obvious respects, all without departing from the spirit and the scope of the present invention. Accordingly, the drawings and detailed description are to be regarded as illustrative in nature and not as restrictive.

BRIEF DESCRIPTION OF THE DRAWINGS

FIG. 1 is a front anatomical diagram showing, by way of example, placement of an implantable vagus stimulation device in a male patient, in accordance with one embodiment.

FIGS. 2A and 2B are diagrams respectively showing the implantable neurostimulator and the simulation therapy lead of FIG. 1.

FIG. 6 is a graph showing, by way of example, a Cheyne-Stokes respiration pattern.

DETAILED DESCRIPTION

Figure 3:
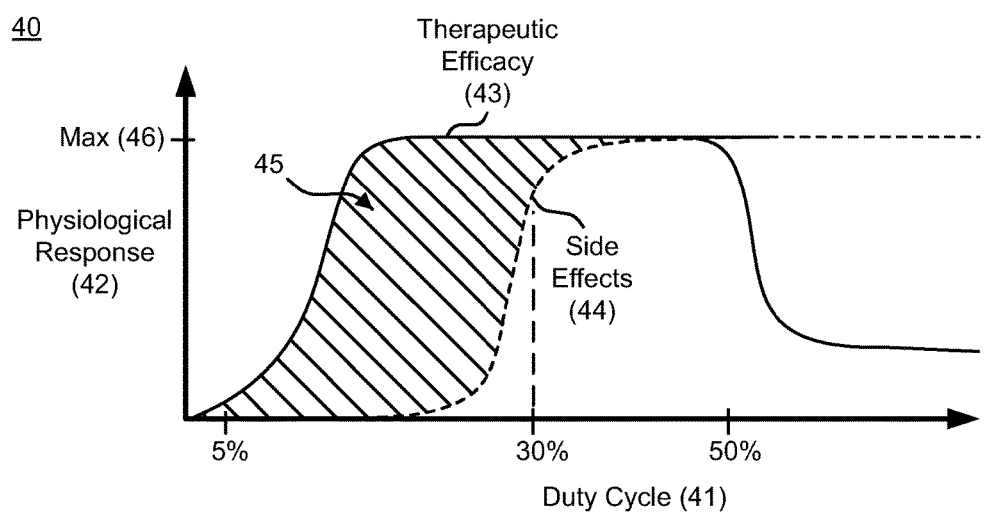
FIG. 3 is a graph showing, by way of example, the relationship between the targeted therapeutic efficacy and the extent of potential side effects resulting from use of the implantable neurostimulator of FIG. 1.

The autonomic nervous systems of patients suffering from various forms of CCD, including CHF, and related cardiovascular diseases exhibit increased sympathetic and decreased parasympathetic central outflow. This imbalance is accompanied by a pronounced elevation of basal heart rate arising from chronic sympathetic hyperactivation along the neurocardiac axis, which is exacerbated by Cheyne-Stokes respiration, a type of CSA common to patients suffering from CHF or stroke, and during NREM sleep during which a period of naturally-occurring bradyarrhythmia can be followed by tachyarrhythmia as breathing stops, blood oxygen level decreases and blood carbon dioxide level increases.

Low intensity peripheral neurostimulation therapies that target the imbalance of the autonomic nervous system have been shown to improve clinical outcomes in patients treated for three to twelve months. Bi-directional autonomic regulation therapy results in simultaneous creation and propagation of efferent and afferent action potentials within the vagus nerve. In contrast to conventional approaches to VNS, the neurostimulation is delivered bi-directionally and at an intensity that is insufficient to elicit pathological or acute physiological side effects, such as acute cardiac arrhythmias, and without the requirement of an enabling physiological feature or triggering physiological marker, such as heart rate or heart rate variability (HRV), such as for purposes of timing stimulation delivery, to confirm therapeutic effect, or other ends. Here, upon continuously-cycling, intermittent and periodic low intensity stimulation of the cervical vagus nerve, action potentials propagate away from the stimulation site in two directions, efferently toward the heart to influence the intrinsic cardiac nervous system and the heart and afferently toward the brain to influence central elements of the nervous system.

The low intensity neurostimulation therapy works to directly restore autonomic balance by engaging both medullary and cardiovascular reflex control components of the autonomic nervous system. The therapy is delivered through an implantable vagus nerve stimulator with, in one embodiment, an integrated heart rate sensor, such as used to treat drug-refractory epilepsy and depression, which can be adapted for use in managing chronic cardiac dysfunction during episodes of Cheyne-Stokes respiration and NREM sleep through low intensity bi-directional vagal stimulation. FIG. 1 is a front anatomical diagram showing, by way of example, placement of an implantable vagus nerve stimulation (VNS) device 11 in a male patient 10, in accordance with one embodiment. The VNS provided through the stimulation device 11 operates under several mechanisms of action. These mechanisms include increasing parasympathetic outflow and inhibiting sympathetic effects by blocking norepinephrine release. More importantly, VNS triggers the release of acetylcholine (ACh) into the synaptic cleft, which has beneficial anti-arrhythmic, anti-apoptotic, and ectopy-reducing anti-inflammatory effects.

The implantable vagus stimulation device 11 includes at least three implanted components, an implantable neurostimulator 12, a therapy lead 13, and helical electrodes 14. The implantable vagus stimulation device 11 can be remotely accessed following implant through an external programmer by which the neurostimulator 12 can be remotely checked and programmed; an external magnet for basic patient control; and an electromagnetic controller that enables the patient 10 to exercise increased control over therapy titration, delivery and suspension. The neurostimulator 12 is preferably interrogated prior to implantation and throughout the therapeutic period with a healthcare provider-operable external programmer and programming wand (not shown) for checking proper operation, downloading recorded data, diagnosing problems, and programming operational parameters. Generally, use of the external programmer is restricted to healthcare providers, while more limited manual control is provided to the patient through "magnet mode." In one embodiment, the external programmer executes application software specifically designed to interrogate the neurostimulator 12. Together, the implantable vagus stimulation device 11 and one or more of the external components form a VNS therapeutic delivery system.

The neurostimulator 12 is implanted in the patient's right or left pectoral region generally on the same side (ipsilateral) as the vagus nerve 15, 16 to be stimulated, although other neurostimulator-vagus nerve configurations, including contra-lateral and bi-lateral are possible. The helical electrodes 14 are generally implanted on the vagus nerve 15, 16 about halfway between the clavicle 19a-b and the mastoid process. The therapy lead 13 and helical electrodes 14 are implanted by first exposing the carotid sheath and chosen vagus nerve 15, 16 through a latero-cervical incision on the ipsilateral side of the patient's neck 18. The helical electrodes 14 are then placed onto the exposed nerve sheath and tethered. A subcutaneous tunnel is formed between the respective implantation sites of the neurostimulator 12 and helical electrodes 14, through which the therapy lead 13 is guided to the neurostimulator 12 and securely connected.

The stimulation device 11 bi-directionally (simultaneously in both afferent and efferent directions) stimulates the vagus nerve 15, 16 through multimodal application of continuously-cycling, intermittent and periodic electrical stimuli. The stimulation is selectively delivered or suspended in response to episodes of Cheyne-Stokes respiration, and during NREM sleep in response to arrhythmias. In a further embodiment, tachyarrhythmias during wakefulness can be managed through application of a boost dose of VNS upon the sensing of a condition indicative of tachyarrhythmias, such as described in commonly-assigned U.S. patent application, entitled "Implantable Neurostimulator-Implemented Method for Managing Tachyarrhythmias through Vagus Nerve Stimulation," Ser. No. 13/673,766, filed on Nov. 9, 2012, pending, the disclosure of which is incorporated by reference. In a still further embodiment, bradycardia in VNS-titrated patients can be managed through suspension of on-going low-level VNS.

Both sympathetic and parasympathetic nerve fibers are stimulated, but at an intensity that is insufficient to elicit acute physiological or acute physiological side effects and without the requirement of an enabling physiological feature or triggering physiological marker. Cervical vagus nerve stimulation results in propagation of action potentials from the site of stimulation in a manner that results in creation and propagation (simultaneously in both afferent and efferent directions) of action potentials within neuronal fibers comprising the cervical vagus nerve to restore cardiac autonomic balance. Afferent action potentials propagate toward the parasympathetic nervous system's origin in the medulla in the nucleus ambiguus, nucleus tractus solitarius, and the dorsal motor nucleus, as well as towards the sympathetic nervous system's origin in the intermediolateral cell column of the spinal cord. Efferent action potentials propagate toward the heart 17 to activate the components of the heart's intrinsic nervous system. Either the left or right vagus nerve 15, 16 can be stimulated by the stimulation device 11. The right vagus nerve 16 has a moderately lower stimulation threshold than the left vagus nerve 15 for heart rate affects at the same parametric levels.

The VNS therapy is delivered autonomously to the patient's vagus nerve 15, 16 through three implanted components that include a neurostimulator 12, therapy lead 13, and helical electrodes 14. FIGS. 2A and 2B are diagrams respectively showing the implantable neurostimulator 12 and the simulation therapy lead 13 of FIG. 1. In one embodiment, the neurostimulator 12 can be adapted from a VNS Therapy AspireSR Model 105 or Model 106 pulse generator, manufactured and sold by Cyberonics, Inc., Houston, Tex., although other manufactures and types of single-pin receptacle implantable VNS neurostimulators with or without integrated leadless heart rate sensors could also be used. The stimulation therapy lead 13 and helical electrodes 14 are generally fabricated as a combined assembly and can be adapted from a Model 302 lead, PerenniaDURA Model 303 lead, or PerenniaFLEX Model 304 lead, also manufactured and sold by Cyberonics, Inc., in two sizes based on helical electrode inner diameter, although other manufactures and types of single-pin receptacle-compatible therapy leads and electrodes could also be used.

Referring first to FIG. 2A, the neurostimulator 12 provides programmed multimodal vagal stimulation. The neurostimulator 12 includes an electrical pulse generator that is tuned to restore autonomic balance by triggering action potentials that propagate bi-directionally (both afferently and efferently) within the vagus nerve 15, 16. The neurostimulator 12 is enclosed in a hermetically sealed housing 21 constructed of a biocompatible, implantation-safe material, such as titanium. The housing 21 contains electronic circuitry 22 powered by a primary battery 23, such as a lithium carbon monoflouride battery. The electronic circuitry 22 is implemented using complementary metal oxide semiconductor integrated circuits that include a microprocessor controller that executes a control program according to stored stimulation parameters and timing cycles; a voltage regulator that regulates system power; logic and control circuitry, including a recordable memory 29 within which the stimulation parameters are stored, that controls overall pulse generator function, receives and implements programming commands from the external programmer, or other external source, collects and stores telemetry information, processes sensory input, and controls scheduled and sensory-based therapy outputs; a transceiver that remotely communicates with the external programmer using radio frequency signals; an antenna, which receives programming instructions and transmits the telemetry information to the external programmer; and a reed switch 30 that provides remote access to the operation of the neurostimulator 12 using an external programmer, a simple patient magnet, or an electromagnetic controller. The recordable memory 29 can include both volatile (dynamic) and persistent (static) forms of memory, such as firmware within which the stimulation parameters and timing cycles can be stored. Other electronic circuitry and components are possible.

Externally, the neurostimulator 12 includes a header 24 to securely receive and connect to the therapy lead 13. In one embodiment, the header 24 encloses a receptacle 25 into which a single pin for the therapy lead 13 can be received, although two or more receptacles could also be provided, along with the requisite additional electronic circuitry 22.

The header 24 internally includes a lead connector block (not shown) and a set of set screws 26.

In one embodiment, the housing 21 can also contain a heart rate sensor 31 that is electrically interfaced with the logic and control circuitry, which receives the patient's sensed heart rate or, alternatively, HRV, as sensory inputs. In a further embodiment, the heart rate sensor 31 is either external to or physically separate from the neurostimulator 12 proper, but is operatively coupled, either through physical wired connection or via wireless interface. The heart rate sensor 31 monitors heart rate or HRV using an ECG-type electrode. Through the electrode, the patient's heart beat can be sensed by detecting ventricular depolarization or similar physiology. In a further embodiment, a plurality of electrodes can be used to sense voltage differentials between electrode pairs, which can undergo signal processing for further cardiac physiological measures, for instance, detection of the P-wave, QRS complex, and T-wave. The heart rate sensor 31 provides the sensed heart rate or HRV to the control and logic circuitry as sensory inputs that can be used to monitor whether the patient 10 is asleep or awake and determine the presence of arrhythmias, especially VT.

In a further embodiment, the housing 21 contains a minute ventilation sensor 32 that is electrically interfaced with the logic and control circuitry, which receives the patient's respiratory dynamics as sensory inputs. In a further embodiment, the minute ventilation sensor 32 is either external to or physically separate from the neurostimulator 12 proper, but is operatively coupled, either through physical wired connection or via wireless interface. The minute ventilation sensor 32, such as described in U.S. Pat. No. 7,092,757, issued Aug. 15, 2006, to Larson et al., the disclosure of which is incorporated by reference, measures the patient's respiratory rate and tidal volume, and calculates the patient's minute ventilation volume. In a yet further embodiment, other forms of metabolic sensors could be used either in combination with or in lieu of the minute ventilation sensor 32 for identifying changes in the patient's physiology, such as temperature, respiratory rate, and the like. The minute ventilation sensor 32 provides the minute ventilation volume to the control and logic circuitry as sensory inputs that can be used to determine whether the patient is asleep, awake, or as an indication of physical activity level, hyperventilation, or hypoventilation.

In a still further embodiment, the housing 21 contains at least one accelerometer 33 that is electrically interfaced with the logic and control circuitry, which can receive the patient's physical movement, posture or orientation as sensory inputs. In a yet further embodiment, the accelerometer 33 is either external to or physically separate from the neurostimulator 12 proper, but is operatively coupled, either through physical wired connection or via wireless interface. In a still further embodiment, the minute ventilation sensor 32 may be combined into a blended sensor with at least one accelerometer 33.

The accelerometer 33 contains the circuitry and mechanical components necessary to measure acceleration, movement or orientation of the patient's body along at least two axes, and may include multiple uniaxial accelerometers, a dual axial accelerometer, or a triaxial accelerometer. By measuring the acceleration along multiple axes, the accelerometer 33 provides sensory inputs that can be used to determine the patient's posture or orientation and rate of movement, which are indicative of activity level and whether the patient has fallen asleep or awakened. In a further embodiment, the accelerometer 33 can determine the patient's activity level and posture, for example, upright versus recumbent, which can be used to determine sleep state. For instance, a low level of activity combined with either a reclined or prone posture would indicate that the patient is asleep. Also, the angle of the patient during sleep can be indicative of the severity of a heart failure condition. This angle during sleep could be used to adjust the intensity or duty cycle of the maintenance dose.

Specifically, the following approaches of combining activity level with posture could be used:

If the posture angle of the patient 10 is less than about 45 degrees (relative to horizontal) and the patient's activity level is below a pre-defined threshold, then the patient can be considered to be asleep.

Upon detection of sleep, the maintenance dose may be reduced or suspended to prevent nighttime bradycardia. This suspension may be applied in addition to a temporary suspension in response to detected bradycardia.

Detection of sleep posture may be used to determine the severity of the patient's heart failure. A greater sleep posture angle (relative to horizontal) may be the result of orthopnea, which may indicative of a more severe heart failure condition. Such a detection could be used to increase the intensity of the daytime maintenance dose.

Referring next to FIG. 2B, the therapy lead 13 delivers an electrical signal from the neurostimulator 12 to the vagus nerve 15, 16 via the helical electrodes 14. On a proximal end, the therapy lead 13 has a lead connector 27 that transitions an insulated electrical lead body to a metal connector pin 28. During implantation, the connector pin 28 is guided through the receptacle 25 into the header 24 and securely fastened in place using the set screws 26 to electrically couple the therapy lead 13 to the neurostimulator 12. On a distal end, the therapy lead 13 terminates with the helical electrode 14. In one embodiment, the lead connector 27 is manufactured using silicone and the connector pin 28 is made of stainless steel, although other suitable materials could be used, as well. The insulated lead body 13 utilizes a silicone-insulated alloy conductor material.

Preferably, the helical electrodes 14 are placed over the cervical vagus nerve 15, 16 at the location below where the superior and inferior cardiac branches separate from the cervical vagus nerve. In alternative embodiments, the helical electrodes may be placed at a location above where one or both of the superior and inferior cardiac branches separate from the cervical vagus nerve. In one embodiment, the helical electrodes 14 are positioned around the patient's vagus nerve oriented with the end of the helical electrodes 14 facing the patient's head. In an alternate embodiment, the helical electrodes 14 are positioned around the patient's vagus nerve 15, 16 oriented with the end of the helical electrodes 14 facing the patient's heart 17. The polarity of the electrodes could be configured into a monopolar cathode, a proximal anode and a distal cathode, or a proximal cathode and a distal anode.

The triggering of CHF compensatory mechanisms, specifically, the chronic sympathetic hyperactivation accompanying a CCD condition, significantly increases the risk of tachyarrhythmias. Moreover, such risk is heightened when the patient is suffering from both CHF and CSA, where the co-occurrence of hypoxaemia and hypercapnia during apneic episodes increases heart rate and causes follow-on hyperventilation as the patient resumes breathing. Similar heightened risk to CHF patients is also presented by nocturnal occurrence of bradyarrhythmias followed by the potential for sequela tachyarrhythmic events. To counter these risks, the VNS is delivered as a multimodal set of therapeutic and event-based doses, which are system output behaviors that are pre-specified within the neurostimulator 12 through the stored stimulation parameters and timing cycles implemented in firmware programming and executed by the microprocessor controller. The selections of therapeutic dose and duty cycle are a tradeoff among competing medical considerations. FIG. 3 is a graph 40 showing, by way of example, the relationship between the targeted therapeutic efficacy 43 and the extent of potential side effects 44 resulting from use of the implantable neurostimulator 12 of FIG. 1. The x-axis represents the duty cycle 41. The y-axis represents relative quantified physiological response 42 to VNS therapy. The neurostimulation is delivered bi-directionally and at an intensity that is insufficient to elicit pathological or acute physiological side effects, such as acute cardiac arrhythmias, and without the requirement of an enabling physiological feature or triggering physiological marker, such as heart rate or HRV.

The duty cycle 41 is determined by dividing the stimulation ON time by the sum of the ON and OFF times of the neurostimulator 12 during a single ON-OFF cycle. In a further embodiment, the stimulation time can include ramp-up and ramp-down times respectively preceding and following the ON time during which the neurostimulator 12 delivers the VNS at full output current, such as further described infra with reference to FIG. 4. Ramp-up and ramp-down times may be necessary, for instance, when the stimulation frequency exceeds a minimum threshold. The physiological response 42 can be expressed quantitatively for a given duty cycle 41 as a function of the targeted therapeutic efficacy 43 and the extent of potential side effects 44. The maximum level ("max") 46 of physiological response 42 signifies the highest point of targeted therapeutic efficacy 43 or potential side effects 44.

The therapeutic efficacy 43 represents the intended effectiveness of VNS in provoking a beneficial physiological response, which may be patient- or population-dependent. In contrast to conventional feedback-driven VNS approaches that require an enabling physiological feature to gauge stimuli delivery efficacy, the acute responses and chronic contributing factors need not be (and are likely not) directly observed contemporaneous to VNS delivery. Rather, the contributing factors could be clinically measured over time, such as in-clinic during patient follow up via ECG trace or other metric. As well, in on-going laboratory studies involving canines, increased heart beat regularity during VNS on time, as exhibited through decreased heart rate variability, has been creditably detected through 24-hour Holter monitoring during vagal neural stimulation at a constant continuously-cycling level below a subcardiac threshold, above which there is a slowing of heart rate, conduction velocity or other cardiac artifact.

The therapeutic efficacy 43 can be quantified by assigning values to the realized acute and chronic responses, which together contribute to and synergistically produce the beneficial physiological response. Acute responses include realized changes in HRV, increased coronary flow, reduction in cardiac workload through vasodilation, and improvement in left ventricular relaxation. Chronic factors include improved cardiovascular regulatory function, decreased negative cytokine production, increased baroreflex sensitivity, increased respiratory gas exchange efficiency, favorable gene expression, renin-angiotensin-aldosterone system down-regulation, anti-arrhythmic, anti-apoptotic, and ectopy-reducing anti-inflammatory effects. Still other acute responses and chronic factors are possible.

Beneficial physiological response is generally also considered to be patient dependent, whereby certain of the contributing factors may be more important for one patient as compared to other patients, and no single contributing factor is fully dispositive or conclusive of whether the physiological response is beneficial for any given patient. The contributing factors can be combined in any manner to quantify the relative level of therapeutic efficacy 43, including weighting particular factors more heavily than others, by tailoring the importance of each contributing factor on a patient-specific or population-specific manner, or applying statistical or numeric functions based directly on or derived from realized changes to the patient's physiology. For example, therapeutic goals of achieving an increase of HRV of 10% and decreased negative cytokine production of 3% may be desired for a particular patient with equal weight assigned to each of these goals. Maximum physiological response 46 occurs when these goals are substantially met.

Empirically, therapeutic efficacy 43 steeply increases beginning at around a 5% duty cycle (patient-dependent), as beneficial physiological response 42 is realized, and levels off in a plateau near the maximum level 46 of physiological response 42 at around a 30% duty cycle (patient-dependent), although some patients may require higher (or lower) duty cycles to show similar beneficial physiological response 42. Thereafter, therapeutic efficacy 43 begins decreasing at around a 50% duty cycle (patient-dependent) and continues in a plateau near a 25% physiological response (patient-dependent) through the maximum 100% duty cycle.

The physiological response and occurrence of side effects to different combinations of VNS parameters and timing cycles has been empirically evaluated in pre-clinical work on canines Like the therapeutic efficacy 43, side effects 44 may be patient- or population-dependent and can be quantified by assigning values to the realized acute and chronic side effects. For example, benign acute side effects, such as coughing, could be assigned a low value, while pathological side effects, like bradycardia, could be rated significantly higher to reflect level of severity. In the canine study, the only side effects that were observed were coughing and throat irritation, retching, and bradycardia and heart block during 4-6 weeks of gradual titration. Following titration, the only remaining side effect that was observed was bradycardia, which was observed in the following ranges:

Right VNS: In an awake animal, bradycardia was typically observed beginning at approximately 1.25-1.5 mA at a pulse width of 500 μsec and approximately 1.5-1.75 mA at a pulse width 250 μsec, independent of stimulation frequency. However, the magnitude of the current-dependent bradycardia increased with stimulation frequency, with the highest level of bradycardia observed at 20 Hz, the lowest level observed at 10 Hz, and an intermediate level observed at 15 Hz. During sleep, bradycardia was observed at similar parameters as in an awake animal.

Left VNS: In an awake animal, bradycardia was only observed at amplitudes greater than 2.5 mA, and primarily in the 3.0-3.5 mA range. Stimulation frequencies of 15 or 20 Hz were more likely to produce bradycardia at the lower end of that amplitude range, and a stimulation frequency of 10 Hz was more likely to produce bradycardia only at the upper end of the range. In some animals, no bradycardia was observed at any combination of parameters up to the maximum stimulation current of 3.5 mA. During sleep, bradycardia was observed at similar parameters to right VNS.

Comparable ranges of side effects in humans are expected.

Figure 4:
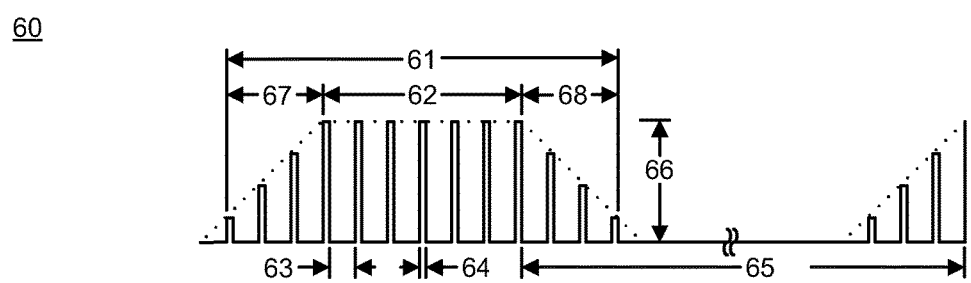
FIG. 4 is a timing diagram showing, by way of example, a stimulation cycle and an inhibition cycle of VNS as provided by implantable neurostimulator of FIG. 1.

In the absence of patient physiology of possible medical concern, such as acute cardiac arrhythmias, VNS is delivered in therapeutic doses that each use alternating cycles of stimuli application (ON) and stimuli inhibition (OFF) that are tuned to activate both afferent and efferent pathways. Stimulation results in parasympathetic activation and sympathetic inhibition, both through centrally-mediated pathways and through efferent activation of preganglionic neurons and local circuit neurons. FIG. 4 is a timing diagram showing, by way of example, a stimulation cycle and an inhibition cycle of VNS 60 as provided by implantable neurostimulator 12 of FIG. 1. The stimulation parameters enable the electrical stimulation pulse output by the neurostimulator 12 to be varied by both amplitude (output current 66) and duration (pulse width 64). The set of stimulation parameters and timing cycle used depends upon the operating mode of therapy desired, that is, maintenance, sleep, or boost, as further described below with reference to FIG. 8. The number of output pulses delivered per second determines the signal frequency 63. In one embodiment, a pulse width in the range of 100 to 250 μsec is used to deliver between 0.02 and 50 mA of output current at a signal frequency of about 20 Hz, although other therapeutic values could be used as appropriate.

In the simplest case, the stimulation time equals the time period during which the neurostimulator 12 is ON and delivering pulses of stimulation. The OFF time 65 equals the time period occurring in-between stimulation times 61 during which the neurostimulator 12 is OFF and inhibited from delivering stimulation. In one embodiment, the neurostimulator 12 implements either or both of a ramp-up time 67 and a ramp-down time 68 that respectively precede and follow the ON time 62 during which the neurostimulator 12 is ON and delivering pulses of stimulation at the full output current 66. The ramp-up time 67 and ramp-down time 68 are used when the stimulation frequency is at least 10 Hz, although other minimum thresholds could be used, and both ramp-up and ramp-down times 67, 68 last two seconds, although other time periods could also be used. The ramp-up time 67 and ramp-down time 68 allow the strength of the output current 66 of each output pulse to be gradually increased and decreased, thereby avoiding deleterious reflex behavior due to sudden delivery or inhibition of stimulation at a full-strength programmed level of intensity.

Figure 5:
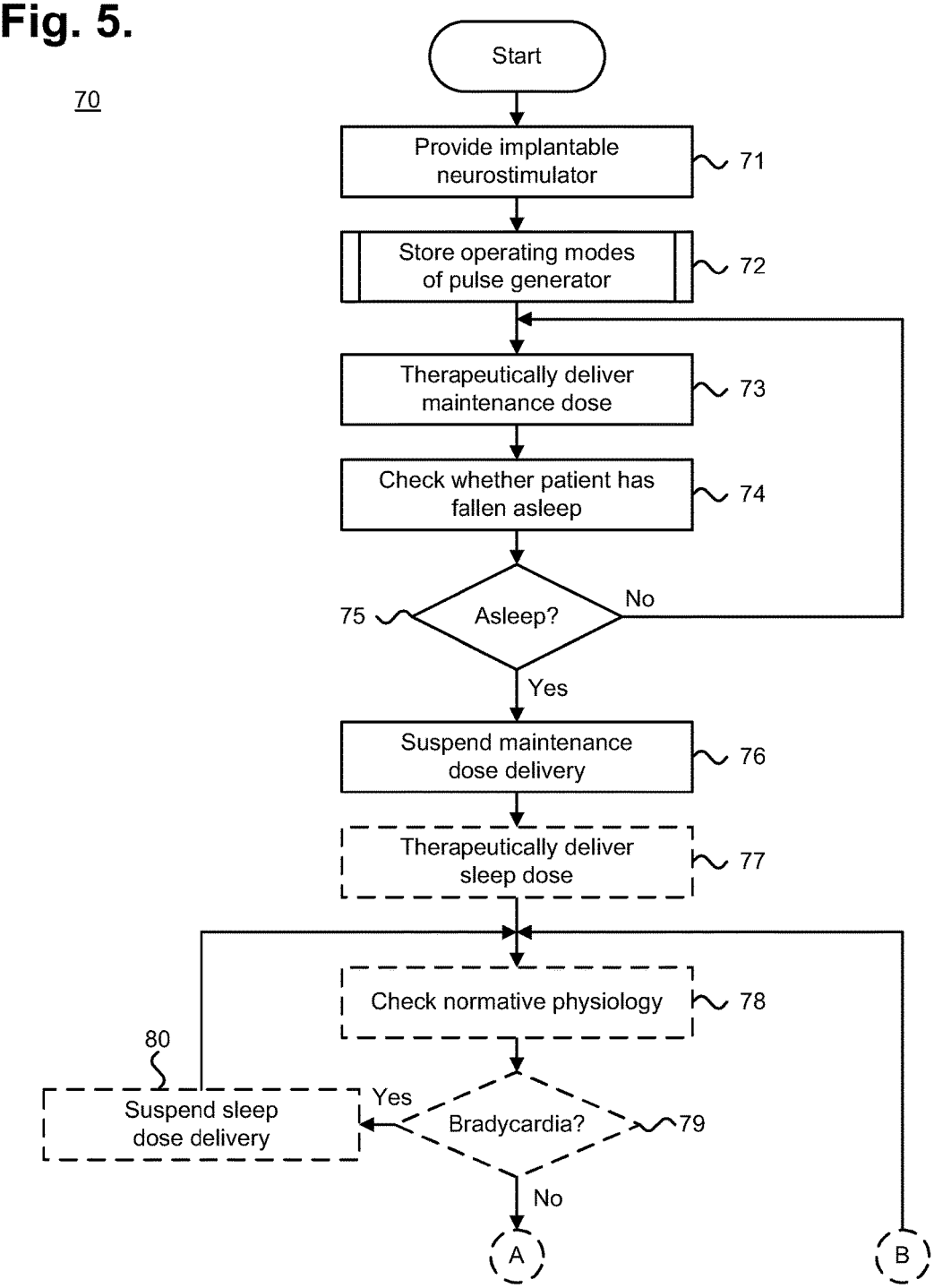
FIG. 5 is a flow diagram showing an implantable neurostimulator-implemented method for managing sleep disorder-related tachyarrhythmias through vagus nerve stimulation, in accordance with one embodiment.

Cardiac arrhythmogenic risk in a patient suffering from some form of CCD during sleep or due to a sleep-related disorder, such as CSA, can be ameliorated through multi-modal VNS therapy. FIG. 5 is a flow diagram showing an implantable neurostimulator-implemented method for managing sleep disorder-related tachyarrhythmias through vagus nerve stimulation 70, in accordance with one embodiment. The method 70 is implemented on the stimulation device 11, the operation of which is parametrically defined through stored stimulation parameters and timing cycles. The method 70 can be used for treatment of both CHF patients and for non-CHF patients suffering from other forms of CCD or related disorders.

In one embodiment, at least three operating modes are stored, which include a maintenance dose, a sleep dose, and an enhanced or "boost" dose. The maintenance dose delivers stimulation at an intensity that is insufficient to elicit pathological or acute physiological side effects and without the requirement of an enabling physiological feature or triggering physiological marker. Nevertheless, low intensity therapeutic VNS can ameliorate pathological tachyarrhythmias in some patients. Further, although VNS has been shown to decrease defibrillation threshold, VNS will not terminate VF in the absence of defibrillation. Rather, VNS prolongs ventricular action potential duration, and so may be effective in extinguishing VT. In addition, the effect of VNS on the AV node may be beneficial in patients with AF by slowing conduction to the ventricles and controlling ventricular rate.

An implantable neurostimulator 12, in combination with at least one physiological or metabolic sensor, such as an integrated heart rate sensor 31, minute ventilation sensor 32, accelerometer 33, blended sensor, or other type of sensing mechanism for measuring the patient's physiology, metabolism, or activity level, is provided (step 71). The neurostimulator 12 includes a pulse generator 11, a nerve stimulation therapy lead 13, and a pair of helical electrodes 14. In a further embodiment, electrodes may be implanted with no implanted neurostimulator or leads. Power may be provided to the electrodes from an external power source and neurostimulator through wireless RF or inductive coupling. Such an embodiment may result in less surgical time for implantation and decreased trauma to the patient.

Figure 8:
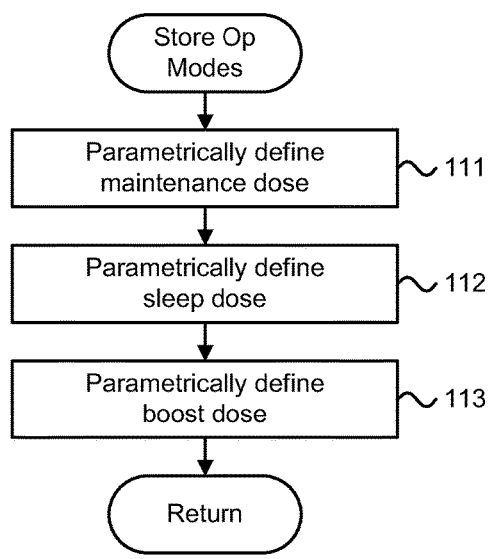
FIG. 8 is a flow diagram showing a routine for storing operating modes for use with the method of FIG. 5.

The pulse generator stores a set of one or more operating modes (step 72) that parametrically define at least three operating modes of the stimulation, including a sleep dose, a maintenance dose delivered at a higher intensity than the sleep dose, and a boost dose delivered at a higher intensity than the maintenance dose, as further described infra with reference to FIG. 8. The neurostimulator 12 delivers therapeutic VNS under control of the electronic circuitry 22, as programmed by the stored stimulation parameters and timing cycles. Each parameter can be independently programmed to define the characteristics of the cycles of therapeutic stimulation and inhibition to ensure optimal stimulation for a patient 10. The programmable stimulation parameters include output current, signal frequency, pulse width, signal ON time, signal OFF time, magnet activation (for VNS specifically triggered by "magnet mode"), and reset parameters. Other programmable parameters are possible. In a further embodiment, sets or "profiles" of preselected stimulation parameters can be provided to physicians, which can be selected with the assistance of an external programmer and fine-tuned to a patient's physiological requirements prior to being programmed into the neurostimulator 12 following implant.

Ordinarily, the maintenance dose is therapeutically delivered to the patient while the patient is awake (step 73), absent other reasons to suspend delivery, such as onset of pathological bradycardia. Additionally, in some patients, the maintenance dose is delivered throughout periods of both wakefulness and sleep. An awake patient's physiological, metabolic or physical state, depending upon the form of sensor used, is regularly monitored to determine whether the patient 10 has fallen asleep (step 74). In one embodiment, heart rate (or HRV) is used to check the patient's physiology using the heart rate sensor 31. A normative heart rate during sleep is generally considered to fall between 60 to 70 beats per minute (bpm). While awake, the heart rate generally falls somewhere under 100 bpm, depending upon patient age, condition and physiology. When the heart rate sensor 31 is used, the normative heart rate of the patient 10 is monitored and recorded periodically to determine whether the patient 10 has fallen asleep.

In general, falling asleep is characterized by the gradual onset of decreased heart rate, blood pressure, cardiac output, arterial baroreceptor set point, systemic vascular resistance, and lower HRV, which, in combination with the heart rate sensor 31, can be detected by the neurostimulator 12, as well as by evaluation of rhythm stability or related rate and rhythm morphological indicators, such as conventionally used in cardiac rhythm management devices. If the heart rate of the patient 10 gradually declines below the mean normative heart rate level recorded while awake, for instance, a heart rate that gradually decreases over a seven-minute period and is then maintained for a non-transitory period of time, the patient 10 is considered to be asleep. In contrast, an abrupt onset of decreased heart rate could be indicative of a bradycardia and not sleep.

In a further embodiment, a minute ventilation sensor 32 can be used to sense sleeping. Minute ventilation is closely tied to heart rate (and HRV) during sleep, as ventilatory volume (tidal volume) and breathing frequency (respiratory rate) decrease synchronously, as does heart rate (and HRV), as the patient falls asleep, then settles into a regular pattern. Tidal volume at rest is measured by the minute ventilation sensor 32. In general, tidal volume at rest is around 0.5 L/min and can increase up to 3.0 L/min at a higher intensity level of exertion. Similarly, respiratory rate at rest is measured by the minute ventilation 32. In general, respiratory rate at rest is around 12 to 16 breathes/min and can increase 40 to 50 breathes/min during maximum levels of activity. A normative activity level while awake can be established, for instance, by taking means of the tidal volume and respiratory rate. If tidal volume and respiratory rate of the patient 10 respectively fall below the mean resting values of tidal volume and respiratory rate, the patient 10 can be considered to be asleep. In a still further embodiment, the heart rate sensor 31 can be used in combination with the minute ventilation sensor 32.

In a still further embodiment, an accelerometer 33 can be used to identify periods of sleep and wakefulness. A normative activity level while awake can be established, for instance, by sensory inputs that can be used to determine the patient's posture and rate of movement. If the patient assumes a recumbent posture and the rate of three-dimensional movement significantly decreases, the patient 10 can be considered to be asleep.

In a yet further embodiment, the neurostimulator 12 can use a multiple forms of sensory data in determining whether the patient 10 is asleep. For instance, the accelerometer 33 can be used in combination with the minute ventilation sensor 32 as a blended sensor, which can correlate patient activity level with respiratory response. Still other measures and indications of patient sleeping and wakefulness are possible. As well, the neurostimulator 12 can assign more weight to one type of sensory data over other types of sensory data. For example, more weight can be assigned to accelerometer 33 data, which would discount a rise in heart rate that occurs while the patient 10 remains recumbent and otherwise still. Other ways of preferentially weighting the data are possible.

If the physiological, metabolic or physical state indicates that the patient 10 has not fallen asleep (step 75), the delivery of the maintenance dose (step 73) normally continues and patient's state is checked periodically (step 74). If the monitored state is indicative of the patient 10 having fallen asleep (step 75), the delivery of the maintenance dose is ordinarily suspended (step 76) for two reasons. First, heart rate naturally decreases during sleep. Delivery of the maintenance dose can be cumulative to the body's natural nocturnal reduction in heart rate and needlessly depletes the neurostimulator's primary battery 23 or other onboard power source. Second, suspending the maintenance dose avoids potentially causing bradycardia by continuing therapy into a period of naturally decreased heart rate during which further reduction of heart rate is undesirable.

Following the suspension of the maintenance dose delivery (step 76), as applicable, a set of optional VNS therapeutic protocols can be followed. One set of protocols (steps 78-82) addresses bradyarrhythmia followed by tachyarrhythmia as occurring during NREM sleep, while a second set of protocols (steps 83-84) deals with CSA and, in particular, episodes of Cheyne-Stokes respiration. Still other sets of sleep- and non-sleep-related protocols are possible.

While asleep, the patient's normative physiology is periodically monitored (step 78). In one embodiment, VNS stimulation remains suspended throughout the period of sleep, absent a tachyarrhythmic episode, which ensures that VNS therapy, particularly delivery of the maintenance dose, will not contribute to or possibly cause bradyarrhythmias. In a further embodiment, a sleep dose of VNS is delivered in place of the maintenance dose (step 77). The sleep dose is parametrically defined as a lower intensity form of the maintenance dose, as further described infra with reference to FIG. 8, and is delivered during the patient's sleep, particularly during NREM sleep, to help further restoration of cardiac autonomic balance. The sleep dose is both preventative and precautionary. Even though heart rate (and HRV) naturally drops during sleep, heart rate (and HRV) could also therapeutically decrease in response to the sleep dose delivery.

The first set of protocols (steps 78-82) applies during NREM sleep. Throughout the period of sleep, the patient's normative physiology while sleeping is assessed for a presence of a condition indicative of sinus bradycardia or sinus pause (step 79). During NREM sleep, a decreased heart rate develops as sympathetic activation is naturally withdrawn, and, in response, benign sinus bradycardia and sinus pauses normally occur. However, patients suffering from CHF or other forms of CCD face an increased risk of experiencing bradyarrhythmia, with follow-on hyperventilation as the body reacts to decreased blood oxygen level. In turn, the hyperventilation can trigger tachyarrhythmic episodes. As an initial precaution, the optional delivery of the sleep dose, if applicable, is suspended (step 80). The patient's normative physiology is also evaluated for a presence of a condition indicative an onset of possible tachyarrhythmia (step 81). For instance, if heart rate significant increases, say, in excess of 180 bpm or more, the patient 10 may be suffering an onset of a tachyarrhythmia. If appropriate, a boost dose of therapeutic VNS is then delivered (step 82), as further described infra with reference to FIG. 7.

The second set of protocols (steps 83-84) deals with the type of CSA known as Cheyne-Stokes respiration, which is most commonly associated with CHF or stroke. FIG. 6 is a graph showing, by way of example, a Cheyne-Stokes respiration pattern 90. The x-axis represents time 91. The y-axis represents respiration amplitude 92. Cheyne-Stokes respiration is characterized by periodic episodes of central apnea 93 and hyperpnea 95, which is interleaved between gradual waxing 97 and waning 98 of tidal volume. The condition can occur at any time, both during sleep and when awake. During each apneic episode 93, breathing stops 94 entirely for about 30 seconds to two minutes, which causes an increase in blood carbon dioxide level. Thereafter, breathing gradually resumes with compensatory hyperventilation 96 followed by gradual cessation, which obversely causes a decrease in blood carbon dioxide level. The oscillation in blood carbon dioxide levels seems to prompt the cyclic swings between apnea and hyperventilation.

The definitive physiological affect of Cheyne-Stokes respiration on CCD is unsettled, yet the condition does appear to exacerbate the excessive sympathetic nervous system activity that accompanies CHF due to apnea-related hypoxia and arousals from sleep, and the characteristic hyperventilation and low blood oxygen levels occurring in Cheyne-Stokes respiration would seem to contribute to a presumptively increased risk of tachyarrhythmia. Referring back to FIG. 5, The patient's normative physiology is evaluated for periodic breathing patterns indicative of Cheyne-Stokes respiration (step 83), using, for instance, a minute ventilation sensor 32. If presented, a boost dose of therapeutic VNS is then delivered (step 84), as further described infra with reference to FIG. 7. Note that in distinction to the first set of protocols (steps 78-82), the second set of protocols (steps 83-84) focus primarily on respiratory response, and not necessarily heart rate (or HRV) as an indicator of therapeutic intervention.

Figure 7:
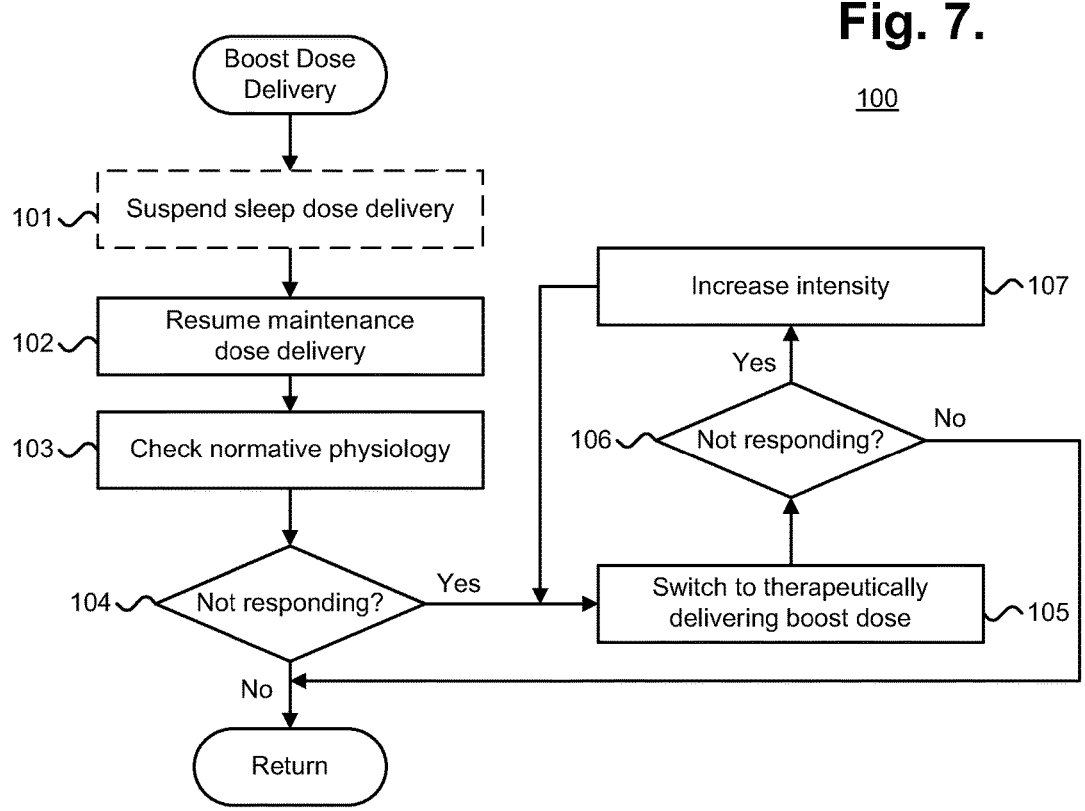
FIG. 7 is a flow diagram showing a routine for delivering a boost dose in response to an occurrence of tachyarrhythmia for use with the method of FIG. 5.

In CHF patients, tachyarrhythmias are of grave concern due to the increased potential for AF, VT, VF, and atrial flutter. The boost dose is delivered at a higher intensity than the maintenance dose and is intended to "break" the tachyarrhythmic condition. FIG. 7 is a flow diagram showing a routine 100 for delivery a boost dose in response to an occurrence of tachyarrhythmia for use with the method 70 of FIG. 5. In addition to the potential of bradyarrhythmia followed by tachyarrhythmia as occurring during NREM sleep, both obstructive and central sleep apneas can also potentially trigger arrhythmias. OSA is caused by an occlusion of the upper airways, with the sequela hypoxia being capable of triggering bradyarrhythmias. The patient makes strenuous ventilatory efforts during an apneic episode, and a significant spike in peripheral sympathetic activity occurs as the hypoxia worsens. In a CHF patient, the sympathetic spike can trigger tachyarrhythmia upon resumption of respiration. Similarly, patients with CSA, which is caused by central ventilatory control defects, experience an increased heart rate (and HRV) during periods of hyperpnea that follow apneic episodes and are consequentially at increased risk of developing tachyarrhythmias upon resumption of respiration. Delivery of the boost dose is intended to respond to all of these conditions.

If a sleep dose was being delivered to the patient 10, the sleep dose is suspended (step 101). Delivery of the maintenance dose is resumed (step 102). Recall that the maintenance dose, even though delivered at an intensity that is insufficient to elicit pathological or acute physiological side effects and without the requirement of an enabling physiological feature or triggering physiological marker, works to directly restore autonomic balance by engaging both medullary and cardiovascular reflex control components of the autonomic nervous system, so resuming delivery of the maintenance dose as an initial response to the possible occurrence of tachyarrhythmia is appropriate.

Thereafter, the patient's normative physiology is periodically checked (step 103). If the potential tachyarrhythmic condition is responding to the VNS stimulation (step 104), the routine 100 ends with the delivery of the maintenance dose resumed. However, if the condition is not responding (step 104), the patient 10 may be suffering onset of a tachyarrhythmia and a higher intensity boost dose of VNS that is tuned to prevent initiation of or disrupt tachyarrhythmia is delivered (step 105), such as described in commonly-assigned U.S. patent application, entitled "Implantable Neurostimulator-Implemented Method for Managing Tachyarrhythmias through Vagus Nerve Stimulation," cited supra. Non-responsiveness can occur due to continuing heart rate elevation, which can present as no appreciable change in heart rate (or HRV), insufficient heart rate (or HRV) decrease, or non-transitory increase in heart rate. More generally, the onset or presence of pathological tachyarrhythmia can be determined by heart rate or rhythm, as well as rhythm stability, onset characteristics, and similar rate and rhythm morphological indicators, as conventionally detected in cardiac rhythm management devices, such as described in K. Ellenbogen et al., "Clinical Cardiac Pacing and Defibrillation," Ch. 3, pp. 68-126 (2d ed. 2000), the disclosure of which is incorporated by reference.

If the tachyarrhythmia is not responding to the boost dose delivery after multiple checks (step 106), the intensity of the boost dose is gradually increased (step 107). Depending upon the patient's heart response trajectory, the intensity of the boost dose can be progressively increased by the same or similar amount each cycle (step 105-107), or for life-threatening or paroxysmal arrhythmias, a stronger boost dose of significantly higher intensity can be used right away (step 105), due to the lack of time to progressively ramp up the intensity. In one embodiment, the stronger boost dose delivery maximizes the VNS stimulation by delivering the maximum intensity of stimulation that the neurostimulator 12 can produce, that is, at full output current or capacity.

In a still further embodiment, delivery of the boost dose, as well as the stronger boost dose, can be manually triggered, increased, decreased, or suspended by providing the neurostimulator 12 with a magnetically-actuated reed switch, which can be triggered by the patient 10 using an external magnet, electromagnetic controller, or similar device. In addition, the delivery of the sleep dose, boost dose, and the maintenance dose can also be manually triggered or swapped. For instance, the reed switch can be triggered by the patient 10 when the maintenance dose is tolerable, while the boost dose is intolerable. Other uses of the switch are possible.

The recordable memory 29 in the electronic circuitry 22 of the neurostimulator 12 (shown in FIG. 2A) stores the stimulation parameters that programmatically control the overall functionality of the pulse generator 11 in providing VNS therapy. FIG. 7 is a flow diagram showing a routine 90 for storing operating modes for use with the method 70 of FIG. 5. At least three operating modes are stored, which include a maintenance dose of VNS tuned to restore cardiac autonomic balance (step 101) through continuously-cycling, intermittent and periodic electrical pulses. The autonomic regulation therapy is provided in a low level maintenance dose independent of cardiac cycle to activate both parasympathetic afferent and efferent neuronal fibers in the vagus nerve. The neurostimulation in the maintenance dose is delivered bi-directionally and at an intensity that is insufficient to elicit pathological or acute physiological side effects and without the requirement of an enabling physiological feature or triggering physiological marker. In one embodiment, in the maintenance dose, a pulse width in the range of 250 to 500 μsec delivering between 0.02 and 1.0 mA of output current at a signal frequency in the range of 5 to 20 Hz, and a duty cycle of 5 to 30%, although other therapeutic values could be used as appropriate.

In contrast, conventional approaches to delivering VNS rely on pulse stimulation of an intensity that is sufficiently strong to "coerce" a behavioral modification of the subject's physiology, that is, directly producing a physiological effect, or the measurement of an enabling physiological feature, such as for purposes of timing stimulation delivery, to confirm therapeutic effect, or other ends. For instance, Sabbah et al., cited supra, discloses preferential stimulation of efferent vagus nerve fibers leading to the heart while blocking afferent neural impulses to the brain using unidirectional activation with an output current in the range of 1-2 mA required to elicit the potentially beneficial effect of vagal stimulation. They observe that a higher output current, while desirable to recruit a larger proportion of B-type nerve fibers, is not feasible due to side effects. Moreover, they caution that non-unidirectional vagal stimulation of lower threshold fibers could lead to uncontrolled effects arising from propagation of neural activation towards the cranium. Similarly, Craig, cited supra, Craig discloses synchronization of vagus nerve stimulation with a physiological cycle, such as the cardiac or respiratory cycle, of a patient. They suggest that the efficacy of the exogenous electrical signal may be improved if the pulses are triggered while the patient is performing paced breathing. Thus, as based on a correlation between respiration-related HRV, electrical stimulation is applied to the vagus nerve at a selected point in the physiological cycle correlated with increased afferent conduction (and not correlated with increased efferent conduction) on the vagus nerve.

In addition, a sleep dose, tuned to a lower intensity than the maintenance dose, is defined (step 102). In one embodiment, the sleep dose uses a pulse width in the range of 250 to 500 μsec delivering between 0.01 and 0.2 mA of output current at a signal frequency in the range of 5 to 20 Hz, and a duty cycle of 5 to 30%, although other therapeutic values could be used as appropriate.

Finally, a boost dose, tuned to prevent initiation of or disrupt tachyarrhythmia, is defined (step 103) through periodic electrical pulses delivered at higher intensity than both the maintenance and sleep doses. Different boost doses can be provided to respond to different tachyarrhythmic events. The boost dose settings are physician-programmable. In one embodiment, for a default boost dose, the stimulation parameters would be in the same range as the maintenance dose, but would be moderately higher, with a pulse width again in the range of 250 to 500 μsec delivering between 1.5 and 2.0 mA of output current at a signal frequency in the range of 5 to 20 Hz. The duty cycle may change significantly from nominally 10% to temporarily 50% or 100%, although other therapeutic values could be used as appropriate. For non-life-threatening or non-paroxysmal tachyarrhythmias, the intensity of the boost dose is progressively increased over time by increasing output current, duty cycle, or frequency, lengthening pulse width, or through a combination of the foregoing parameters. Discretely-defined boost doses, each using different parameters sets, may be delivered in the course of treating a single continuing tachyarrhythmic event, such as for life-threatening or paroxysmal arrhythmias that rapidly generate and require a significantly stronger boost dose with no ramp up time.

In a further embodiment, the suspension and resumption of the maintenance, sleep, and boost doses can be titrated as applicable to gradually withdraw or introduce their respective forms of VNS.

While the invention has been particularly shown and described as referenced to the embodiments thereof, those skilled in the art will understand that the foregoing and other changes in form and detail may be made therein without departing from the spirit and scope.

What is claimed is:

1. An implantable neurostimulator-implemented method for managing tachyarrhythmic risk accompanying central sleep apnea through vagus nerve stimulation, comprising the steps of:

providing an implantable neurostimulator comprising a pulse generator configured to deliver electrical therapeutic stimulation in a manner that results in creation and propagation (simultaneously in both afferent and efferent directions) of action potentials within neuronal fibers comprising a patient's cervical vagus nerve;

storing operating modes of the pulse generator in a recordable memory, comprising:

parametrically defining a maintenance dose of the electrical therapeutic stimulation tuned to restore cardiac autonomic balance through continuously-cycling, intermittent and periodic electrical pulses at an intensity that avoids acute physiological side effects and with an unchanging cycle not triggered by physiological markers; and parametrically defining a boost dose of the electrical therapeutic stimulation tuned to prevent initiation of or disrupt tachyarrhythmia through periodic electrical pulses delivered at higher intensity than the maintenance dose;

therapeutically delivering the maintenance dose to the vagus nerve independent of cardiac cycle via a pulse generator comprised in the implantable neurostimulator through at least a pair of helical electrodes electrically coupled to the pulse generator via a nerve stimulation therapy lead; and monitoring the patient's physiological state via at least one sensor comprised in the implantable neurostimulator, and upon sensing a pattern indicative of Cheyne-Stokes respiration, delivering the boost dose to the vagus nerve via the pulse generator through the pair of helical electrodes.

2. A method according to claim 1, further comprising the steps of:

monitoring the patient's physiological state while awake via at least one sensor comprised in the implantable neurostimulator; and upon sensing that the patient is asleep, suspending the delivery of the maintenance dose.

3. A method according to claim 1, further comprising the steps of:

upon sensing the pattern indicative of Cheyne-Stokes respiration, initially resuming the delivery of the maintenance dose prior to the delivery of the boost dose.

4. A method according to claim 1, further comprising the steps of:

providing a minute ventilation sensor as the at least one sensor;

periodically sensing the patient's tidal volume and respiratory rate with the minute ventilation sensor; and confirming that the pattern is indicative of Cheyne-Stokes respiration when the patient's tidal volume and respiratory rate gradually wax, peak and wane in a periodic pattern.

5. A method according to claim 1, further comprising the step of:

progressively intensifying the electrical therapeutic stimulation as specified in the operating mode of the boost dose as the condition indicative of tachyarrhythmia continues.

6. A method according to claim 5, further comprising the step of:

maximizing the intensity of the electrical therapeutic stimulation as specified in the operating mode when the condition indicative of tachyarrhythmia fails to respond to the intensified electrical therapeutic stimulation.

7. A non-transitory computer readable storage medium storing code for executing on an implantable neurostimulator to perform the method according to claim 1.

8. An implantable neurostimulator-implemented apparatus for managing tachyarrhythmic risk accompanying central sleep apnea through vagus nerve stimulation, comprising the steps of:
  means for providing an implantable neurostimulator comprising a pulse generator configured to deliver electrical therapeutic stimulation in a manner that results in creation and propagation (simultaneously in both afferent and efferent directions) of action potentials within neuronal fibers comprising a patient's cervical vagus nerve;
  means for storing operating modes of the pulse generator in a recordable memory, comprising:
    means for parametrically defining a maintenance dose of the electrical therapeutic stimulation tuned to restore cardiac autonomic balance through continuously-cycling, intermittent and periodic electrical pulses at an intensity that avoids acute physiological side effects and with an unchanging cycle not triggered by physiological markers; and
    means for parametrically defining a boost dose of the electrical therapeutic stimulation tuned to prevent initiation of or disrupt tachyarrhythmia through periodic electrical pulses delivered at higher intensity than the maintenance dose;
  means for therapeutically delivering the maintenance dose to the vagus nerve independent of cardiac cycle via a pulse generator comprised in the implantable neurostimulator through at least a pair of helical electrodes electrically coupled to the pulse generator via a nerve stimulation therapy lead; and
  means for monitoring the patient's physiological state via at least one sensor comprised in the implantable neurostimulator, and upon sensing a pattern indicative of Cheyne-Stokes respiration, delivering the boost dose to the vagus nerve via the pulse generator through the pair of helical electrodes.

* * * * *